United States Patent
Gopinath

(10) Patent No.: US 11,883,107 B2
(45) Date of Patent: Jan. 30, 2024

(54) STENT PLANNING SYSTEMS AND METHODS USING VESSEL REPRESENTATION OBTAINED VIA INTRAVASCULAR PROBE BY DETERMINING STENT EFFECTIVENESS SCORE AND FRACTIONAL FLOW RESERVE

(71) Applicant: LightLab Imaging, Inc., Westford, MA (US)

(72) Inventor: Ajay Gopinath, Bedford, MA (US)

(73) Assignee: LightLab Imaging, Inc., Westford, MA (US)

( * ) Notice: Subject to any disclaimer, the term of this patent is extended or adjusted under 35 U.S.C. 154(b) by 1172 days.

(21) Appl. No.: 15/718,835

(22) Filed: Sep. 28, 2017

(65) Prior Publication Data
US 2018/0085170 A1   Mar. 29, 2018

Related U.S. Application Data

(60) Provisional application No. 62/400,731, filed on Sep. 28, 2016.

(51) Int. Cl.
*A61B 34/10*  (2016.01)
*A61B 8/12*  (2006.01)
(Continued)

(52) U.S. Cl.
CPC ............ *A61B 34/10* (2016.02); *A61B 5/0084* (2013.01); *A61B 8/06* (2013.01); *A61B 8/0891* (2013.01);
(Continued)

(58) Field of Classification Search
CPC ........................ A61B 34/10; A61B 2034/108
See application file for complete search history.

(56) References Cited

U.S. PATENT DOCUMENTS

| 5,321,501 A | 6/1994 | Swanson et al. |
| 5,459,570 A | 10/1995 | Swanson et al. |

(Continued)

FOREIGN PATENT DOCUMENTS

| JP | 2013505782 A | 2/2013 |
| JP | 2016507280 A | 3/2016 |

(Continued)

OTHER PUBLICATIONS

Migliavacca et al (Virtual bench testing to study coronary bifurcation stenting, EuroIntervention 2015;11:V31-V34).*

(Continued)

*Primary Examiner* — Serkan Akar
(74) *Attorney, Agent, or Firm* — Lerner David LLP

(57) ABSTRACT

In part, the disclosure relates to determining a stent deployment location and other parameters using blood vessel data. Stent deployment can be planned such that the amount of blood flow restored from stenting relative to an unstented vessel increases one or more metrics. An end user can specify one or more stent lengths, including a range of stent lengths. In turn, diagnostic tools can generate candidate virtual stents having lengths within the specified range suitable for placement relative to a vessel representation. Blood vessel distance values such as blood vessel diameter, radius, area values, chord values, or other cross-sectional, etc. its length are used to identify stent landing zones. These tools can use or supplement angiography data and/or be co-registered therewith. Optical imaging, ultrasound, angiography or other imaging modalities are used to generate the blood vessel data.

9 Claims, 15 Drawing Sheets

(51) Int. Cl.
*A61B 8/08* (2006.01)
*A61B 8/00* (2006.01)
*A61B 5/00* (2006.01)
*A61B 8/06* (2006.01)
*A61B 6/00* (2006.01)
*A61B 5/107* (2006.01)
*A61B 34/00* (2016.01)
*G16H 50/50* (2018.01)
*G16H 50/30* (2018.01)
*G06N 20/00* (2019.01)
*G16H 20/40* (2018.01)
*A61F 2/82* (2013.01)

(52) U.S. Cl.
CPC ............... *A61B 8/12* (2013.01); *A61B 8/463* (2013.01); *A61B 8/466* (2013.01); *A61B 8/5223* (2013.01); *G16H 50/30* (2018.01); *G16H 50/50* (2018.01); *A61B 5/0066* (2013.01); *A61B 5/107* (2013.01); *A61B 6/504* (2013.01); *A61B 34/25* (2016.02); *A61B 2034/104* (2016.02); *A61B 2034/105* (2016.02); *A61B 2034/108* (2016.02); *A61F 2/82* (2013.01); *A61F 2240/001* (2013.01); *G06N 20/00* (2019.01); *G16H 20/40* (2018.01)

(56) References Cited

U.S. PATENT DOCUMENTS

| | | |
|---|---|---|
| 5,465,147 A | 11/1995 | Swanson |
| 5,477,858 A | 12/1995 | Norris et al. |
| 5,509,093 A | 4/1996 | Miller et al. |
| 5,531,227 A | 7/1996 | Schneider |
| 5,619,368 A | 4/1997 | Swanson |
| 5,662,109 A | 9/1997 | Hutson |
| 5,748,598 A | 5/1998 | Swanson et al. |
| 5,771,895 A | 6/1998 | Slager |
| 5,784,352 A | 7/1998 | Swanson et al. |
| 5,797,849 A | 8/1998 | Vesely et al. |
| 5,956,355 A | 9/1999 | Swanson et al. |
| 5,989,189 A | 11/1999 | LeBlanc et al. |
| 6,111,645 A | 8/2000 | Tearney et al. |
| 6,134,003 A | 10/2000 | Tearney et al. |
| 6,148,095 A | 11/2000 | Prause et al. |
| 6,160,826 A | 12/2000 | Swanson et al. |
| 6,191,862 B1 | 2/2001 | Swanson et al. |
| 6,208,883 B1 | 3/2001 | Holupka et al. |
| 6,282,011 B1 | 8/2001 | Tearney et al. |
| 6,421,164 B2 | 7/2002 | Tearney et al. |
| 6,445,939 B1 | 9/2002 | Swanson et al. |
| 6,485,413 B1 | 11/2002 | Boppart et al. |
| 6,501,551 B1 | 12/2002 | Tearney et al. |
| 6,552,796 B2 | 4/2003 | Magnin et al. |
| 6,564,087 B1 | 5/2003 | Pitris et al. |
| 6,570,659 B2 | 5/2003 | Schmitt |
| 6,706,004 B2 | 3/2004 | Tearney et al. |
| 6,879,851 B2 | 4/2005 | McNamara et al. |
| 6,891,984 B2 | 5/2005 | Petersen et al. |
| 7,208,333 B2 | 4/2007 | Flanders et al. |
| 7,231,243 B2 | 6/2007 | Tearney et al. |
| 7,241,286 B2 | 7/2007 | Atlas |
| 7,397,935 B2 | 7/2008 | Kimmel et al. |
| 7,414,779 B2 | 8/2008 | Huber et al. |
| 7,415,049 B2 | 8/2008 | Flanders et al. |
| 7,593,559 B2 | 9/2009 | Toth et al. |
| 7,619,646 B2 | 11/2009 | Freifeld et al. |
| 7,625,366 B2 | 12/2009 | Atlas |
| 7,729,746 B2 | 6/2010 | Redel et al. |
| 7,801,343 B2 | 9/2010 | Unal et al. |
| 7,813,609 B2 | 10/2010 | Petersen et al. |
| 7,848,791 B2 | 12/2010 | Schmitt et al. |
| 7,916,387 B2 | 3/2011 | Schmitt et al. |
| 7,935,060 B2 | 5/2011 | Schmitt et al. |
| 8,116,605 B2 | 2/2012 | Petersen et al. |
| 8,206,377 B2 | 6/2012 | Petroff |
| 8,298,147 B2 | 10/2012 | Huennekens et al. |
| 8,325,419 B2 | 12/2012 | Schmitt |
| 8,358,461 B2 | 1/2013 | Huber et al. |
| 8,412,312 B2 | 4/2013 | Judell et al. |
| 8,449,468 B2 | 5/2013 | Petersen et al. |
| 8,478,384 B2 | 7/2013 | Schmitt et al. |
| 8,478,387 B2 | 7/2013 | Xu |
| 8,503,844 B2 | 8/2013 | Petersen et al. |
| 8,581,643 B1 | 11/2013 | Schmitt |
| 8,582,109 B1 | 11/2013 | Schmitt |
| 8,582,619 B2 | 11/2013 | Adler |
| 8,582,934 B2 | 11/2013 | Adler et al. |
| 8,676,299 B2 | 3/2014 | Schmitt et al. |
| 8,687,201 B2 | 4/2014 | Adler |
| 8,753,281 B2 | 6/2014 | Petersen et al. |
| 8,786,336 B1 | 7/2014 | Schmitt |
| 8,831,321 B1 | 9/2014 | Elbasiony |
| 8,902,941 B2 | 12/2014 | Schmitt |
| 8,926,590 B2 | 1/2015 | Petroff |
| 8,948,228 B2 | 2/2015 | Adler |
| 8,948,613 B2 | 2/2015 | Schmitt et al. |
| 8,953,911 B1 | 2/2015 | Xu et al. |
| 8,983,580 B2 | 3/2015 | Boppart et al. |
| 9,007,696 B2 | 4/2015 | Petersen et al. |
| 9,069,396 B2 | 6/2015 | Adler et al. |
| 9,091,524 B2 | 7/2015 | Adler et al. |
| 9,138,147 B2 | 9/2015 | Schmitt et al. |
| 9,164,240 B2 | 10/2015 | Schmitt et al. |
| 9,173,591 B2 | 11/2015 | Elbasiony et al. |
| 9,351,698 B2 | 5/2016 | Dascal et al. |
| 9,404,731 B2 | 8/2016 | Adler et al. |
| 9,417,052 B2 | 8/2016 | Adler |
| 9,435,956 B1 | 9/2016 | Xu et al. |
| 9,462,950 B2 | 10/2016 | Xu |
| 9,488,464 B1 | 11/2016 | Schmitt |
| 9,526,424 B2 | 12/2016 | Judell et al. |
| 9,572,495 B2 | 2/2017 | Schmitt et al. |
| 9,610,064 B2 | 4/2017 | Adler et al. |
| 9,702,687 B2 | 7/2017 | Schmitt |
| 9,702,762 B2 | 7/2017 | Friedman et al. |
| 9,833,221 B2 | 12/2017 | Hutchins et al. |
| 2002/0115931 A1 | 8/2002 | Strauss et al. |
| 2002/0161351 A1 | 10/2002 | Samson et al. |
| 2005/0043614 A1 | 2/2005 | Huizenga et al. |
| 2005/0201662 A1 | 9/2005 | Petersen et al. |
| 2005/0238067 A1 | 10/2005 | Choi |
| 2006/0095065 A1 | 5/2006 | Tanimura et al. |
| 2006/0165270 A1 | 7/2006 | Borgert et al. |
| 2006/0187537 A1 | 8/2006 | Huber et al. |
| 2006/0203859 A1 | 9/2006 | Cable et al. |
| 2006/0241465 A1 | 10/2006 | Huennekens et al. |
| 2006/0244973 A1 | 11/2006 | Yun et al. |
| 2007/0135707 A1 | 6/2007 | Redel et al. |
| 2007/0135803 A1 | 6/2007 | Belson |
| 2007/0293932 A1 | 12/2007 | Zilla et al. |
| 2008/0100612 A1 | 5/2008 | Dastmalchi et al. |
| 2009/0027051 A1 | 1/2009 | Stuber et al. |
| 2009/0174931 A1 | 7/2009 | Huber et al. |
| 2009/0204134 A1 | 8/2009 | Kassab |
| 2009/0306520 A1 | 12/2009 | Schmitt et al. |
| 2010/0076320 A1 | 3/2010 | Petersen et al. |
| 2011/0071404 A1 | 3/2011 | Schmitt et al. |
| 2011/0101207 A1 | 5/2011 | Schmitt |
| 2011/0157686 A1 | 6/2011 | Huber et al. |
| 2011/0190586 A1 | 8/2011 | Kemp |
| 2011/0228280 A1 | 9/2011 | Schmitt et al. |
| 2011/0257545 A1 | 10/2011 | Suri |
| 2012/0075638 A1* | 3/2012 | Rollins ............... A61B 1/00009 356/479 |
| 2012/0238869 A1 | 9/2012 | Schmitt et al. |
| 2012/0250028 A1 | 10/2012 | Schmitt et al. |
| 2012/0300215 A1 | 11/2012 | Johnson et al. |
| 2012/0300216 A1 | 11/2012 | Johnson et al. |
| 2012/0310081 A1 | 12/2012 | Adler et al. |
| 2013/0010303 A1 | 1/2013 | Petersen et al. |
| 2013/0012811 A1 | 1/2013 | Schmitt et al. |
| 2013/0023761 A1 | 1/2013 | Petroff |
| 2013/0051728 A1 | 2/2013 | Petroff |

(56) References Cited

U.S. PATENT DOCUMENTS

| | | |
|---|---|---|
| 2013/0072805 A1 | 3/2013 | Schmitt et al. |
| 2013/0123616 A1 | 5/2013 | Merritt et al. |
| 2013/0303910 A1 | 11/2013 | Hubbard et al. |
| 2013/0310698 A1 | 11/2013 | Judell et al. |
| 2014/0018669 A1 | 1/2014 | Xu |
| 2014/0024931 A1 | 1/2014 | Winston et al. |
| 2014/0094697 A1 | 4/2014 | Petroff et al. |
| 2014/0100449 A1 | 4/2014 | Begin et al. |
| 2014/0114182 A1 | 4/2014 | Petersen et al. |
| 2014/0142427 A1 | 5/2014 | Petroff |
| 2014/0142432 A1 | 5/2014 | Hutchins et al. |
| 2014/0142436 A1 | 5/2014 | Hutchins et al. |
| 2014/0187929 A1 | 7/2014 | Schmitt et al. |
| 2014/0218742 A1 | 8/2014 | Adler |
| 2014/0249407 A1 | 9/2014 | Adler et al. |
| 2014/0268167 A1 | 9/2014 | Friedman et al. |
| 2014/0276011 A1 | 9/2014 | Schmitt et al. |
| 2014/0276020 A1 | 9/2014 | Hutchins et al. |
| 2014/0309526 A1 | 10/2014 | Douk et al. |
| 2014/0379269 A1 | 12/2014 | Schmitt |
| 2015/0153157 A1 | 6/2015 | Schmitt et al. |
| 2015/0119707 A1 | 7/2015 | Schmitt |
| 2015/0192405 A1 | 7/2015 | Schmitt |
| 2015/0297373 A1 | 10/2015 | Schmitt et al. |
| 2015/0370229 A1 | 12/2015 | Adler et al. |
| 2015/0374243 A1 | 12/2015 | Itu et al. |
| 2016/0000406 A1 | 1/2016 | Petroff |
| 2016/0022208 A1 | 1/2016 | Gopinath |
| 2016/0022371 A1 | 1/2016 | Sauer et al. |
| 2016/0058307 A1 | 3/2016 | Svanerudh |
| 2016/0070066 A1 | 3/2016 | Schmitt et al. |
| 2016/0073885 A1 | 3/2016 | Adler |
| 2016/0171711 A1 | 6/2016 | Gopinath et al. |
| 2016/0174925 A1 | 6/2016 | Dascal et al. |
| 2016/0313507 A1 | 10/2016 | Adler et al. |
| 2016/0335763 A1 | 11/2016 | Ambwani et al. |
| 2016/0335766 A1 | 11/2016 | Ambwani et al. |
| 2017/0020392 A1 | 1/2017 | Xu |
| 2017/0024532 A1 | 1/2017 | Gopinath et al. |
| 2017/0024910 A1 | 1/2017 | Griffin et al. |
| 2017/0103520 A1 | 4/2017 | Gopinath et al. |
| 2017/0135663 A1 | 5/2017 | Dascal et al. |
| 2017/0140531 A1 | 5/2017 | Dascal et al. |
| 2017/0140532 A1 | 5/2017 | Dascal et al. |
| 2017/0143296 A1 | 5/2017 | Peterson et al. |
| 2017/0148161 A1 | 5/2017 | Griffin |
| 2017/0188831 A1 | 7/2017 | Adler et al. |
| 2017/0261378 A1 | 9/2017 | Friedman et al. |
| 2017/0301084 A1 | 10/2017 | Gopinath |
| 2017/0325712 A1 | 11/2017 | Gopinath |
| 2018/0003482 A1 | 1/2018 | Schmitt |

FOREIGN PATENT DOCUMENTS

| | | |
|---|---|---|
| JP | 2016508750 A | 3/2016 |
| WO | 2006076409 | 7/2006 |
| WO | 2007002685 | 1/2007 |
| WO | 2011038044 | 3/2011 |
| WO | 2014092755 | 6/2014 |
| WO | 2014092755 A1 | 6/2014 |
| WO | 2015121674 A1 | 8/2015 |
| WO | 2016014991 | 1/2016 |
| WO | 2016014991 A1 | 1/2016 |
| WO | 2016187218 | 11/2016 |
| WO | 2016187218 A1 | 11/2016 |
| WO | 2016187231 | 11/2016 |
| WO | 2016187231 A1 | 11/2016 |

OTHER PUBLICATIONS

Morris et al Virtual Fractional Flow Reserve From Coronary Angiography Modeling the Significance of Coronary Lesions, JACC: Cardiovascular Interventions, vol. 6, No. 2, 2013 (Year: 2013).*

International Search Report and Written Opinion of the International Searching Authority for International Application No. PCT/US2017/054017 mailed from the International Searching Authority dated Feb. 7, 2018 (14 pages).

Wang et al., "Automatic stent strut detection in intravascular optical coherence tomographic pullback runs", The Int J Cardiovasc Imaging, (2013) 29:29-38, (10 pages).

International Search Report and Written Opinion for International application No. PCT/US2016/062213, mailed from the International Searching Authority dated Jan. 30, 2017 (12 pages).

International Search Report and Written Opinion of the International Searching Authority for International Application No. PCT/US2013/029855 dated Jun. 17, 2013 (10 pages).

International Search Report and Written Opinion of the International Search Authority for International patent application No. PCT/US2015/042083 dated Oct. 21, 2015 (9 pages).

Bonnema et al., "An automatic algorithm for detecting stent endothelialization from volumetric optical coherence tomography datasets", Physics in Medicine and Biology, 53:12, Jun. 21, 2008, pp. 3083-3098.

Unal et al., "Stent implant follow-up in intravascular optical coherence tomography images", Int J Cardiovasc Imaging (2010)26:809-816.

Xu et al., "Characterization of atherosclerosis plaques by measuring both backscattering and attenuation coefficients in optical coherence tomogrpahy", Journal of Biomedical Optics, 13:3, May/Jun. 2008, 8 pages.

Takano et al., "Evaluation by Optical Coherence Tomography of Neointimal Coverage of Sirolimus-Eluting Stent Three Months After Implantation", American Journal of Cardiology, vol. 99, No. 8, Apr. 14, 2007, pp. 1033-1038.

International Search Report for International Application No. PCT/US2009/060714, dated Jan. 4, 2010, 6 pages.

Written Opinion of the International Searching Authority for International Application No. PCT/US2009/060714, dated Jan. 4, 2010, 6 pages.

English translation of Japanese Office Action of application 2011-531266 dated Feb. 25, 2014 (6 pages).

* cited by examiner

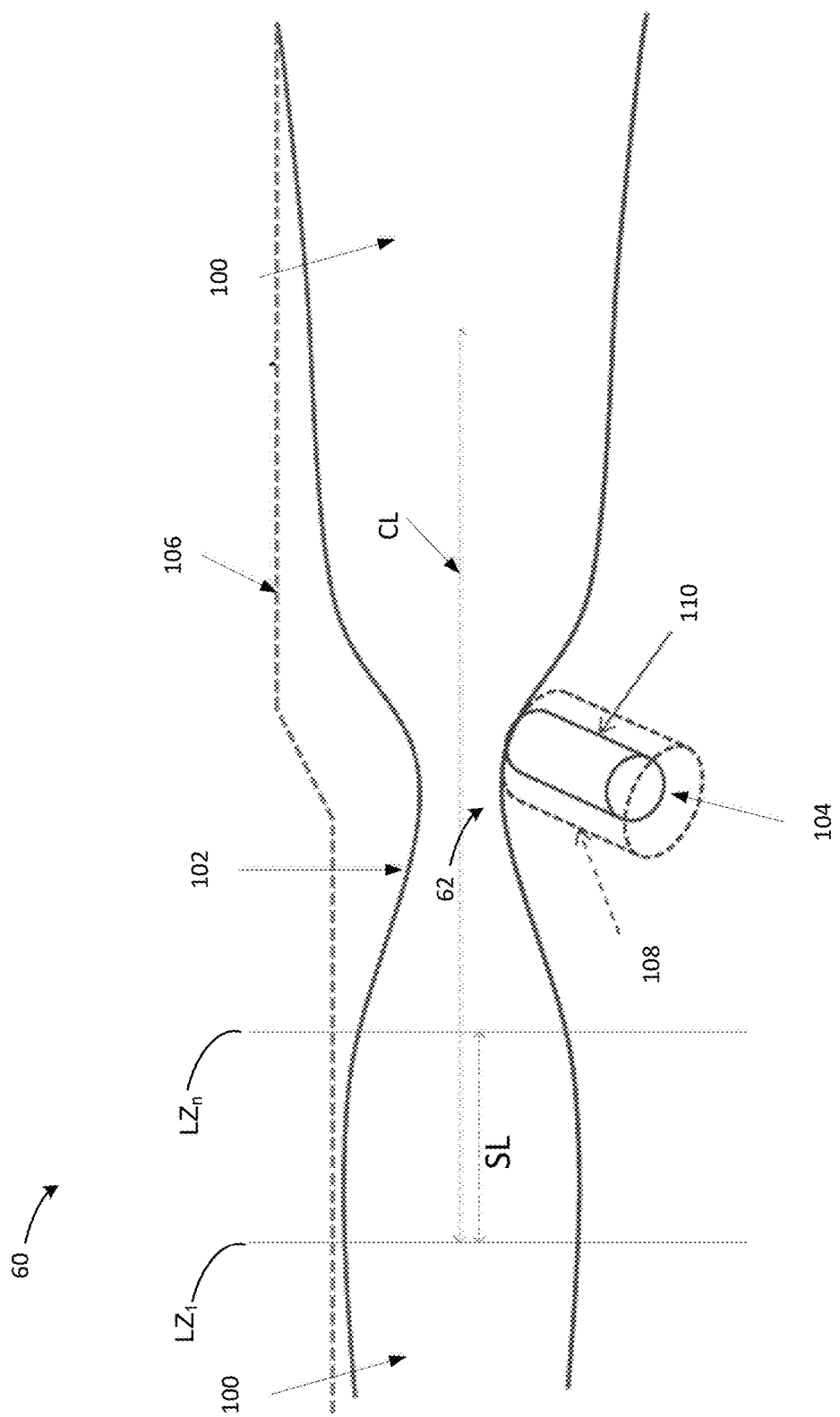

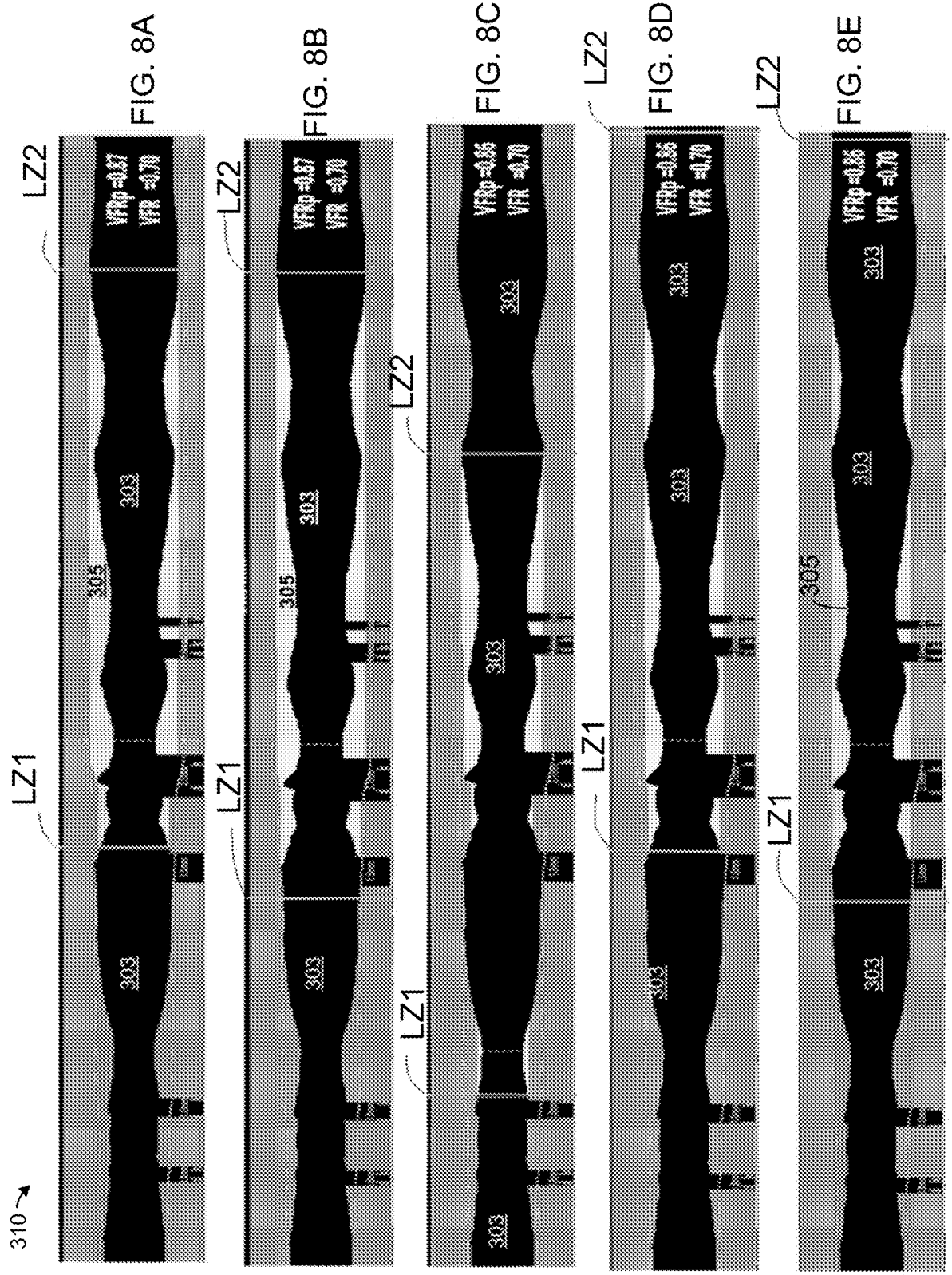

STENT PLANNING SYSTEMS AND METHODS USING VESSEL REPRESENTATION OBTAINED VIA INTRAVASCULAR PROBE BY DETERMINING STENT EFFECTIVENESS SCORE AND FRACTIONAL FLOW RESERVE

CROSS REFERENCE TO RELATED APPLICATIONS

This application claims priority to and the benefit of U.S. Provisional Patent Application No. 62/400,731 filed on Sep. 28, 2016, the disclosure of which is herein incorporated by reference in its entirety.

FIELD

The disclosure relates generally to stent planning. In part, the disclosure relates to diagnostic tools, methods and systems to plan stent deployment relative to a blood vessel representation using collected data.

BACKGROUND

The placement of stents in coronary arteries requires a significant amount of planning. Such planning may be accomplished by the physician with longitudinal photographs of the coronary vessel and a ruler. This has inherent limitations. Further, in the case of complex lesions, the optimal deployment location and stent size cannot be determined from viewing a cross-sectional presentation of the vessel alone. Various factors can change which stent should be used and where it should be placed that are not apparent based on a manual review of images.

Even an experienced cardiologist may find it challenging to predict the stent size to use and selecting a placement location that would result in the best outcome. In addition, given the goal of reducing cath lab time, having tools that accelerate the process and offer advantages over manual approaches are needed. Technologies that allow for automating the placement of stents in an artery, at optimal locations and with shortest sized stent using computer-based user interfaces and vessel representations are needed.

The present disclosure addresses this need and others.

BRIEF SUMMARY

In part, the disclosure relates to determining a stent deployment location and other parameters using blood vessel data. A representation of the blood vessel is generated and displayed via a user interface. Stent deployment can be planned such that the amount of blood flow restored from stenting relative to an unstented vessel increases one or more metrics. An end user can specify one or more stent lengths, including a range of stent lengths. In turn, diagnostic tools can generate candidate virtual stents having lengths within the specified range suitable for placement relative to a vessel representation. Blood vessel distance values such as blood vessel diameter, radius, area values, chord values, or other cross-sectional, etc. its length are used to identify stent landing zones. These tools can use or supplement angiography data and/or be co-registered therewith. Optical imaging, ultrasound, angiography or other imaging modalities are used to generate the blood vessel data.

In one embodiment, the disclosure relates to assessing a blood vessel using a Virtual Fractional Flow Reserve or Virtual Flow Reserve computational flow model. In either case, these can be referred to as VFR. As part of that assessment, the computer-implemented methods facilitate developing stent plan using virtual stenting, based on predicted flow recovery via a cardiovascular system parameter such as for example, VFR. Any suitable cardiovascular system parameter that changes as a result of stent deployment can also be used as a basis for scoring one or more virtual stents. In one embodiment, the systems and methods are designed to emphasize stent length relative to selection process such that a shorter stent is selected while simultaneously achieving a target flow restoration level such as a maximum flow restoration or otherwise increased flow restoration. In one embodiment, a representation of a blood vessel segment is generated based upon blood vessel data such as imaging data, which can include intravascular data or angiography or tomography data. In one embodiment, blood vessel data is obtained with during a pullback of a data collection probe through the actual corresponding vessel segment in a patient.

In part, the disclosure relates to a method of planning deployment of one or more intravascular stents. The method includes storing, in an electronic memory device, blood vessel data collected with regard to a candidate blood vessel for stent deployment; calculating, using a subsystem of an blood vessel data collection system, a set of lumen distance-based values from the blood vessel data, the subsystem in electronic computing with the electronic memory device; identifying a set of local maxima from the set of lumen distance-based values, wherein the local maxima are correlated with potential stent landing zones; determining one or more frames in the blood vessel data corresponding to local maxima; determining a set of candidate stent landing zones by identifying all combinations of pairs of frames disposed at boundary of a search window, wherein a size of search window is a length of one or more stents; and generating, for each pair of candidate landing zones, a stent effectiveness score (SES) that results from placement of a virtual stent of a given distance and length at each pair of candidate landing zones; ordering the stent effectiveness scores; and identifying one or more virtual stents, defined by landing zones determined based on a ranked order of the stent effectiveness scores.

The method may further include displaying the one or more virtual stents relative to a representation of a segment of the blood vessel. The lumen distance-based values may be selected from a group consisting of a lumen area, a lumen radius, a lumen diameter, a lumen chord, and a distance that is measured from a point on a boundary of a lumen. The set of lumen distance-based values may include a lumen area curve. The set of lumen distance-based values may include a set of lumen area values corresponding to cross-sections of the blood vessel. The method may further include generating a representation of a stent having a stent length and displaying the representation of the stent disposed at a first landing zone and a second landing zone, wherein the first and the second landing zone correspond to the stent effectiveness score.

Generating the SES may include one or more of calculating a first virtual fractional flow reserve (VFR) for the vessel prior to placing the stent; calculating a second Virtual Fractional Reserve for the vessel subsequent to placing the stent; subtracting a first VFR from second VFR to obtain a change in VFR in response to stent placement; and dividing the change in VFR by the length of the stent.

The method may further include adjusting the SES with one or more weighting factors. The one or more weighting factors may include one or more of: quality of landing zone;

total lumen area of all branches covered by the stent; amount of tapering of blood vessel; stent limits based on physician preference; and restrictions based on artery type. The method may further include selecting the SES with a predicted VFR above or equal to an end user set target VFR. The method may further include receiving inputs from an end user regarding stent parameter preferences. The method may further include generating a predicted VFR in response to a user selected stent for placement relative to a representation of the blood vessel. The method may further include generating the blood vessel data using angiography or intravascular imaging.

In part, the disclosure relates to a system for automated stent planning. The system may include a diagnostic system to obtain data from a vessel of interest, the diagnostic system may include an electronic memory device; and a processor in communication with the electronic memory device, wherein the memory comprises instructions executable by the processor to cause the processor to: compute, using the processor, a set of lumen distance-based values from intravascular data generated using an intravascular probe pulled back through the blood vessel, the subsystem in electronic computing with the electronic memory device; identify a set of local maxima from the set of lumen distance-based values, wherein one or more local maxima are correlated with potential stent landing zones; determine one or more frames in the intravascular data that correspond to one or more of the local maxima; and determine a set of candidate stent landing zones by identifying one or more frames disposed at a boundary of a search window, wherein a size of search window is a length of one or more stents.

The lumen distance-based values may be selected from a group consisting of a lumen area, a lumen radius, a lumen diameter, a lumen chord, and a distance that is measured from a point on a boundary of a lumen. The system may further include instructions executable by the processor to cause the processor to: generate, for each pair of candidate landing zones, a stent effectiveness score (SES) that results from placement of a virtual stent of a given distance and length at each pair of candidate landing zones; rank the stent effectiveness scores; and identifying one or more virtual stents, defined by landing zones determined based on ranking of the stent effectiveness scores. In one embodiment, the one or more virtual stents are displayed relative to a representation of a segment of the blood vessel.

The system may further include instructions executable by the processor to cause the processor to: generate a representation of a stent having a stent length and displaying the representation of the stent disposed at a first landing zone and a second landing zone, wherein the first and the second landing zone correspond to the stent effectiveness score.

The system may further include instructions executable by the processor to cause the processor to: adjust the SES with one or more weighting factors. The one or more weighting factors may include one or more of: the quality of landing zone; total lumen area of all branches covered by the stent; amount of tapering of blood vessel; stent limits based on physician preference; and restrictions based on artery type. The system may further include instructions executable by the processor to cause the processor to: morph a representation of a vessel using a stent representation to compute a change in an intravascular parameter suitable for determining the SES.

In part, the disclosure relates to a method of planning deployment of one or more intravascular stents. The method includes storing, in an electronic memory device, blood vessel data of a blood vessel generated using an intravascular probe pulled back through the blood vessel; identifying candidate sent landing zones in blood vessel data; determining a set of possible landing zone pairs; scoring virtual stent landing zones based on changes to one or more vascular system parameters, wherein the changes are between stented and unstented state of blood vessel; ranking and selecting score and associated landing zones; and displaying landing zones for virtual stent having selected score.

Software embodiments can include programs, processor instructions, firmware, resident software, micro-code, pseudo code, flow charts steps, etc. Hardware and software may be combined or connected such as through a communication channel, memory, wireless communications and can be generally described as a "circuit," "module" or "system."

The disclosure also relates to computer program product embodied in any tangible medium of expression having computer-usable program code embodied in the medium. The described embodiments may be provided as a computer program product, or software, that may include a machine-readable medium having stored thereon instructions, which may be used to program a computer system (or other computing or other electronic device(s)) to perform a process according to embodiments. A machine-readable medium includes any mechanism for storing or transmitting information in a form (e.g., software, processing application) readable by a machine (e.g., a computer). A machine-readable medium may be a machine-readable storage medium, or a machine-readable signal medium.

Computer program code for carrying out operations of the embodiments may be written in any combination of one or more programming languages, including an object-oriented programming language such as Java, Python, C++ or the like and conventional procedural programming languages, such as the "C" programming language or similar programming languages. The program code may execute entirely on a user's computer, partly on the user's computer, as a stand-alone software package, partly on the user's computer and partly on a remote computer or entirely on the remote computer or server. Matlab and similar software can also be used to implement certain rankings and plots used herein.

Although, the invention relates to different aspects and embodiments, it is understood that the different aspects and embodiments disclosed herein can be integrated together as a whole or in part, as appropriate. Thus, each embodiment disclosed herein can be incorporated in each of the aspects to varying degrees as appropriate for a given implementation. Further, the systems, methods, steps, components, and parts of the foregoing can be used for medical applications and other applications for diagnostic purposes and stent development and analysis.

In one embodiment, the method is implemented using a cluster-based method. For example, a set of candidate landing zones is grouped based on one or more criteria.

Other features and advantages of the disclosed embodiments will be apparent from the following description and accompanying drawings.

BRIEF DESCRIPTION OF THE DRAWINGS

The figures are not necessarily to scale, emphasis instead generally being placed upon illustrative principles. The figures are to be considered illustrative in all aspects and are not intended to limit the invention, the scope of which is defined only by the claims.

FIGS. 3A and 3B are schematic representation of blood vessels showing stent landing zone and flow restoration features in accordance with an illustrative embodiment the disclosure.

FIGS. 8A-8E depict additional user interface views showing blood vessel representations including longitudinal representation of stenosis of cluster 1 of FIG. 7 according to an illustrative embodiment of the invention.

DETAILED DESCRIPTION

Figure 1:
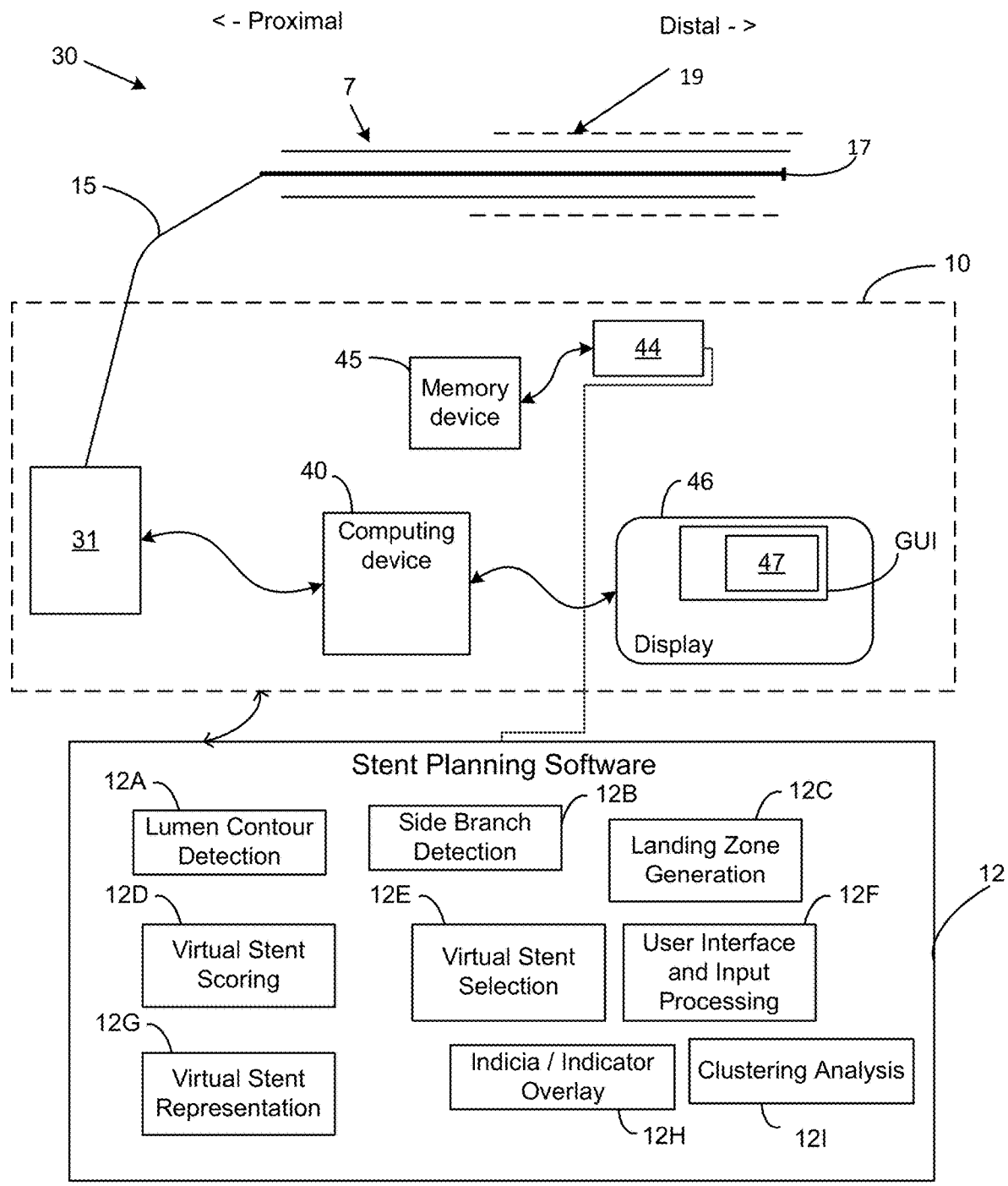
FIG. 1 is a schematic diagram of an intravascular diagnostic/data collection system constructed in accordance with an illustrative embodiment the disclosure.

In part, the disclosure relates to systems and methods for stent planning. The systems and methods described herein are implemented using blood vessel data obtained using a pullback of a data collection device such as an imaging device through an artery. The data collection device is typically an intravascular probe such as an optical coherence tomography (OCT) or intravascular ultrasound (IVUS) probe. The intravascular probe is used in conjunction with a data collection/diagnostic system such as an OCT or IVUS system. The system includes one or more computing devices that access the blood vessel data such as intravascular data stored in one or more electronic memory devices.

In one embodiment, the diagnostic system is used with the intravascular probe can access image data generated using data collected by the probe as it moves through the artery. This image data can be presented using various graphical user interfaces. The diagnostic system can provide various workflows and options to facilitate the process of stent planning relative to the artery imaged during such a pullback. Additionally, the disclosure relates to computer-implemented methods by which a stent effectiveness score (SES) or other metrics can be generated or used to perform stent planning. In one implementation, a score or other metric is assigned to a stent or a stent pair based upon the stent selection and the positions of each stent in the artery. That is, from a set of candidate stents or groups of stents, each set or group is scored or ranked relative to a criteria or score that is reflexive of how the selection and placement of the stent(s) affects a given vascular system parameter or other parameter. These scores can be tied to various vascular system parameters. In general, the scores used to select a candidate stent are referred to herein a stent effectiveness score (SES).

For example, in one embodiment, the SES is designed to account for or track the flow improvement due to one or more of the location of a stent, the size of that stent and the length of the stent. This can be estimated using changes in a parameter as a result of a given candidate virtual stent. In one embodiment, the parameter used for estimating flow changes is Virtual Flow Reserve. Accordingly, in one embodiment, SES=$\Delta$VFR/(Stent Length) wherein $\Delta$VFR is the improvement in the VFR value due the placement of that stent. In one embodiment, stents that are shorter and result in an improvement in VFR will have higher SES values. In this way, SES is designed to reflect the benefit of using shorter stents.

In general, deployment of shorter stents can result in less metal or other material being introduced in the artery. Using smaller stents can result in less trauma given the torturous nature of the arteries and their movement over time such as during various activities by a recipient of the stent. One or more shorter stents is sometimes desirable because they can be positioned to follow the bends of an artery rather one long stent which may apply stress to the artery when the artery bends or moves.

In one embodiment, the one or more cardiovascular or vascular system parameters suitable for generating a SES by which landing zones and the associated virtual can include without limitation a Virtual Flow Reserve (VFR) values, flow velocity, a pressure value, a maximum flow, a minimum flow one or more fractional flow reserve (FFR) values, coronary flow reserve (CFR) values, coronary flow velocity reserve (CFVR) values, instantaneous flow reserve (IFR) values, one or more index of myocardial resistance (IMR) values and a vascular resistance value, a combination of the foregoing, a weighted average of one or more of the foregoing and another value, and values derived from the foregoing. In one embodiment, virtual flow reserve can also refer to virtual fractional flow reserve (VFR). In general, a VFR value can be determined by using an intravascular imaging probe to generate frames of imaging data that segment the artery through a pullback.

In turn, this imagining data and lumen areas and diameters facilitates a volume-based analysis. Further, by using angiography and other parallel sources of data and coupling them, fluid dynamics, and the frames of imaging data vascular system parameters such as VFR can be used to obtain correlation similar to or better than FFR. These parameters can be used with virtual stents, landing zones, clustering-based methods and others methods as described herein to perform stenting planning and other diagnostic and analytic methods.

In one embodiment, the SES for each stent candidate that resulted in a post-stent predicted VFR of greater than about 0.80 or about 0.85 is ranked. These values have been determined from empirical studies as treatment thresholds. In one embodiment, VFR or FFR values range from about 0.7 to about 0.8 are ranking for virtual stent selection given the beneficial expected increase in flow post-stenting. These SES scores are sorted in descending order. The stent candidate with the largest SES from this sorted list can be selected by the system and displayed as a default stent selection for use by an end user. The virtual stent with such an SES score can also be identified to the end user as one option to consider as part of the stent planning process.

To inform and facilitate understanding of the operation of some aspects of the software and methods described herein, it is useful to consider an artery that has a narrowing in the middle, a stenosis, that effectively acts as a bottleneck. An exemplary bottleneck 62, such as from a stenotic lesion or other vessel obstruction, can be seen in FIG. 3A which is discussed in more detail below. Blood flow is reduced at the bottleneck or point of stenosis while proximal and distal areas downstream from the have larger diameters and thus larger cross-sectional areas relative to the contours of the walls of the blood vessel.

Thus, along the blood vessel as measured by the imaging probe during its pullback through the vessel, there are cross-sections of the blood vessel which have diameters of a certain length and associated cross-sectional areas of a certain size such that the diameters and areas are maximized relative to other local cross-sections and lumen diameters in their vicinity. Lumen diameters and lumen cross-sectional areas can effectively be treated interchangeably herein because but for a scaling factor and some changes to the appearance of curves plotting these two parameters, a local maximum for a lumen diameter will match up with a local maximum for a lumen area (and vice versa). Other lumen distance measures can be used without limitation. With this example, it is useful to consider an exemplary planning system.

Referring to FIG. 1, a stent planning system for suggesting stent placement options and implementations of other embodiments includes an intravascular diagnostic system/data collection system 10 that in turn includes an intravascular probe 7. The probe 7 in various embodiments may include other imaging modalities such as, for example, OCT, intravascular ultrasound (IVUS), and others. The probe 7 is in optical communication with an intravascular diagnostic system/data collection system 10. The OCT optical system or subsystem 31 that connects to probe 7 via an optical fiber 15 includes a light source such as a laser, an interferometer having a sample arm and a reference arm, various optical paths, a clock generator, photodiodes, and other OCT system components.

The system 10 further includes one or more diagnostic software tools or modules 12 relating to stent planning. This software can be stored as a non-transitory instruction on one or more memory devices such as memory device 45 and executed by one or more computing devices such as computing device 40. The stent planning software tools can include one or more vessel profiles such as target profiles generated by a user, a comparator or other comparison software routine for comparing pre and post stent profiles or other profiles. The stent profile analysis software 12 can include an overlay method suitable to superimpose the image of a deployed stent relative to a target profile or to otherwise overlay one or more pre or post stent profiles. In general, the software 12 can process a set of intravascular data and carry out the various methods steps described herein such as those described with regard to FIG. 2A, FIG. 2B and FIG. 2C.

The software 12 is designed to operate upon intravascular data sets and other blood vessel data from an intravascular probe or other detector or data source such as an angiography system. In one embodiment, blood vessel data can be recorded during a pullback procedure and stored in an electronic memory device. The software can include various modules or operative components to perform one or more of the processes or methods described herein. The stent planning software 12 can include without limitation one or more of the following software components or modules: Lumen Contour Detection 12A; Side Branch Detection 12B; Landing Zone Generation 12C; Virtual Stent Scoring 12D; Virtual Stent Selection 12E; User Interface and Input Processing 12F; Virtual Stent Representation 12G; Indicia/Indicator Overlay 12H, Clustering Analysis for Overlap Zones 121 and others as described herein with regard to different processes and methods.

In one embodiment, software modules designed to operate upon intravascular data to characterize the tissue and identify regions of interest such as calcium regions, taper regions, lipid pools, and other tissue features can be used to lower a given SES if placement of a landing zone on one of these tissue types or a side branch location is undesirable. The software 12 can also compare Fractional Flow Reserve (FFR), Vascular Resistance Ratio (VRR), and other measured and calculated intravascular data collection parameters. To the extent such parameters change from a stented state to a non-stent state, such parameters can be used to generate one or more SESs.

In one embodiment, an OCT system 31 can be used. The system includes an optical receiver such as a balanced photodiode based system receives light returned by the probe 7. A computing device 40, such as a computer, a processor, an ASIC or other device that is part of the system 10 or is included as a separate subsystem in electrical or optical communication with the system 10 and receives electronic signals from the probe 7. The computing device 40 in various embodiments includes local memory, buses and other components suitable for processing data and utilizing software 44, such as image data processing configured for stent visualization and stent malapposition detection. The stent deployment planning tools 12 can be part of or exchange data with software 44. These tools can be used to place a virtual stent in the lumen area that the probe 7 is disposed in relative to vessel wall. Region 19 shows an exemplary region of a segment of a pullback wherein one or more virtual stents can be deployed and displayed on a user interface.

As shown, in FIG. 1, a display 46 can also be part of the system 10 for showing information 47 such as cross-sectional and longitudinal views of a blood vessel generated using collected intravascular data. Once the intravascular data is obtained with the probe 7 and stored in memory 45, it can be processed to generate and display information 47 such as a cross-sectional, a longitudinal, and/or a three-dimensional view of the blood vessel along the length of the pullback region or a subset thereof. These views can be depicted as part of a user interface as shown and described below and in subsequent figures. The images of the blood vessel generated using the distances measurements obtained from the system 10 provide information about the blood vessel including lumen contours, vessel diameters, vessel cross-sectional areas, landing zones, and a virtual stent bounded by the landing zones when processed using the tools and software modules described herein.

The methods and systems disclosed herewith provide diagnostic and planning tools for a user. For example, the methods and systems include tools such that placement of virtual stents in an artery can be performed automatically relative to image data from a pullback. Further, the automatic placements of such stents include processes, user interface, and related software-based features to display such stents at optimal locations and with the size of a suitable stent identified for an end user.

The disclosure includes various implementations of stent planning software to place a stent at an optimal location or otherwise at a location that optimizes certain parameters. In one embodiment, the parameters optimized to facilitate stent planning include the amount of flow, which can be achieved by deploying a stent of a particular length. The proximal and distal landing zone locations for the stent and the size of the stent are provided to an end user. These are determined by optimizing the improvement in flow that can be achieved using a set of possible stents and stent deployment locations.

As one exemplary approach to evaluating flow restoration as a result of stent deployment, the methods described in U.S. patent application Ser. No. 14/115,527 entitled "METHOD AND APPARATUS FOR AUTOMATED DETERMINATION OF A LUMEN CONTOUR OF A STENTED BLOOD VESSEL," the contents of which are incorporated by reference herein in their entirety, can be used. Other approaches can be used, including as otherwise as recited herein. To understand some aspects relative to flow changes and behaviors in an artery, it is informative to consider the features shown in FIGS. 3A and 3B which show a stenosis and various features relating to the selection and position of virtual stents based on identified landing zones and stent length(s).

The disclosure also provides computer implemented methods for calculating the degree of branch obstruction. In turn, obstructed or narrowed areas that are candidates for stent deployment can be evaluated in their obstructed state and then compared to an unobstructed state as a result of the lumen diameters and associated lumen areas being morphed through the dilation of an area of a vessel from positioning a candidate virtual stent between target landing zones. Several methods can be used to calculate branch obstruction due to the presence of pathology (e.g., stenosis) or medical intervention (e.g., jailing of side branches).

In an embodiment, a reference vessel diameter method is used to assess blood vessel obstruction. FIG. 3A shows a representation of a vessel 60 having a main vessel 100 having a stenosis 102. A side branch 104 also is shown. Using the virtual stent candidate scoring various landing zones for a stent are evaluated. Exemplary landing zones for a stent of stent length SL is shown on the left side of FIG. 3A. A center line CL of the representation of the vessel 60 is also shown.

Figure 3B:
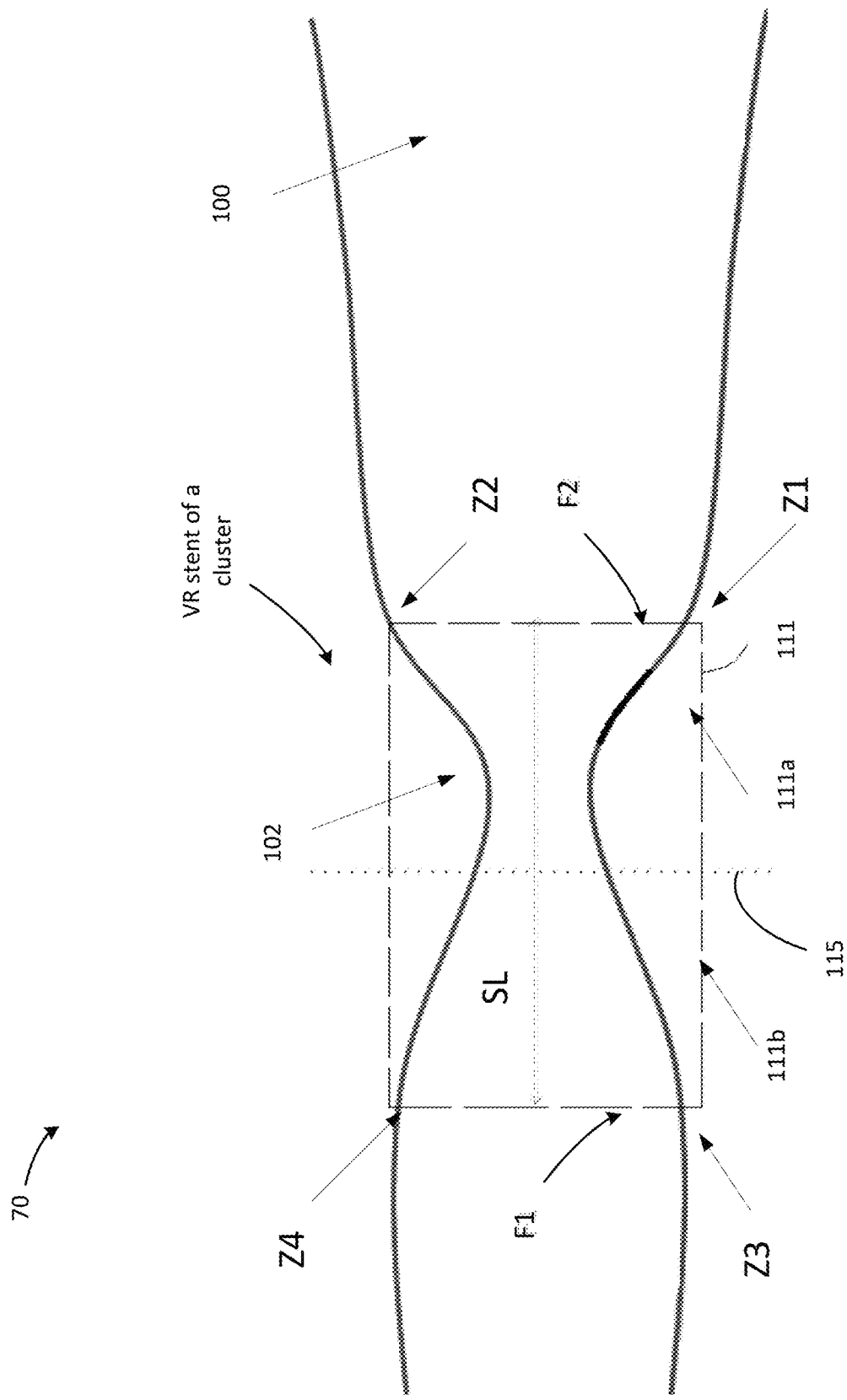

Typically, as shown in a zoomed in view 70 of FIG. 3B of the stenosis 102, one virtual stent 111 can be deployed relative to the stenosis 102 to expand the lumen of the blood vessel. The virtual stent contacts the blood vessel at points Z1 and Z2 on the right side of the figure and points Z4 and Z3 on the left side of the figure. If these two pairs of points are considered as being disposed along a frame, one frame on the left F1 and one frame on the right F2, these frame are examples of those that would be selected as a result of containing a local maximum. The dotted vertical line 115 is included to show that, instead of a single stent 111, two stents can be deployed and select as vertical stents with line 115 being shown as a diving reference line for stents 111a, 111b.

As part of the process of scoring and selecting virtual stents as candidates for deploying in an artery, multiple landing zones are considered for the blood vessel. Thus, for stent 111 shown, it is informative to consider multiple versions of such as stent having the same length SL but shifted to the left and right of frames F1 and F2. These sets of possible landing zones and thus the virtual stents bounded by them can form a cluster that spans a particular subset or region of the blood vessel. Overlapping landing zones can be used to selected preferred landing zones for stent deployment.

Figure 7:
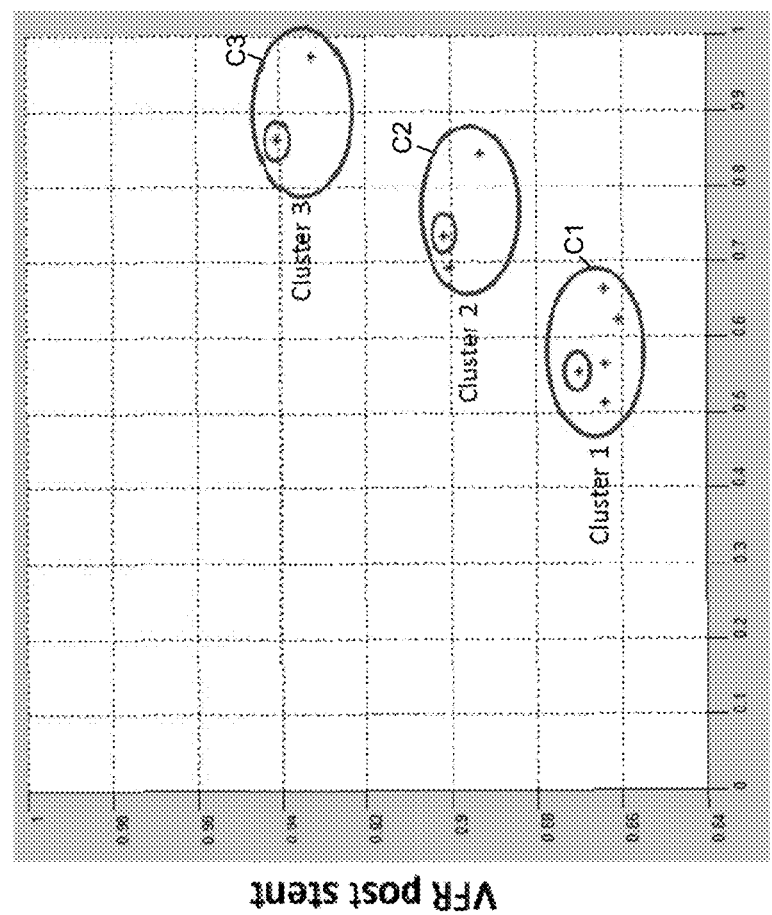
FIG. 7 depicts a plot generated as part of a cluster analysis to identify three clusters as shown in a plot of a parameter that changes post stenting with a virtual stent and the ratio of stent length to pullback length according to an illustrative embodiment of the invention.
Figure 11:
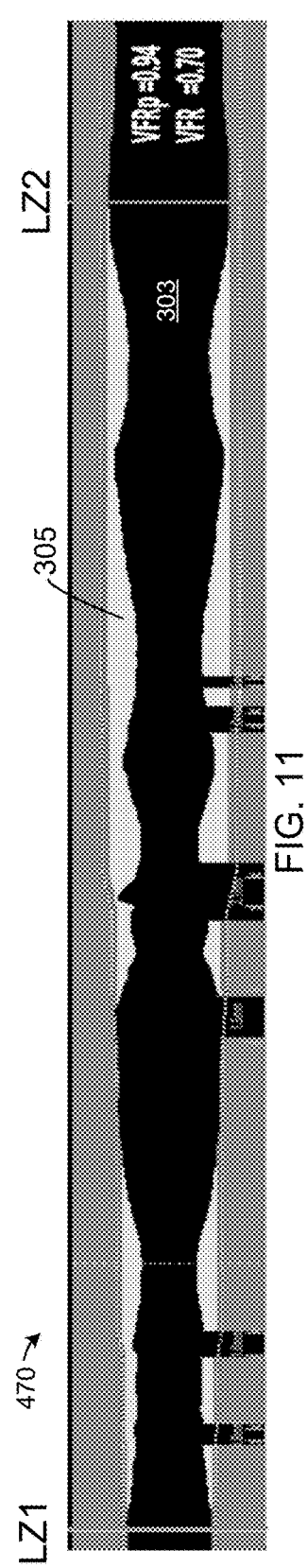
FIG. 11 is a lumen profile view corresponding to a vessel representation showing the overlapping regions of cluster 3 from FIG. 7 and FIG. 10 according to an illustrative embodiment of the invention.
Figure 12A:
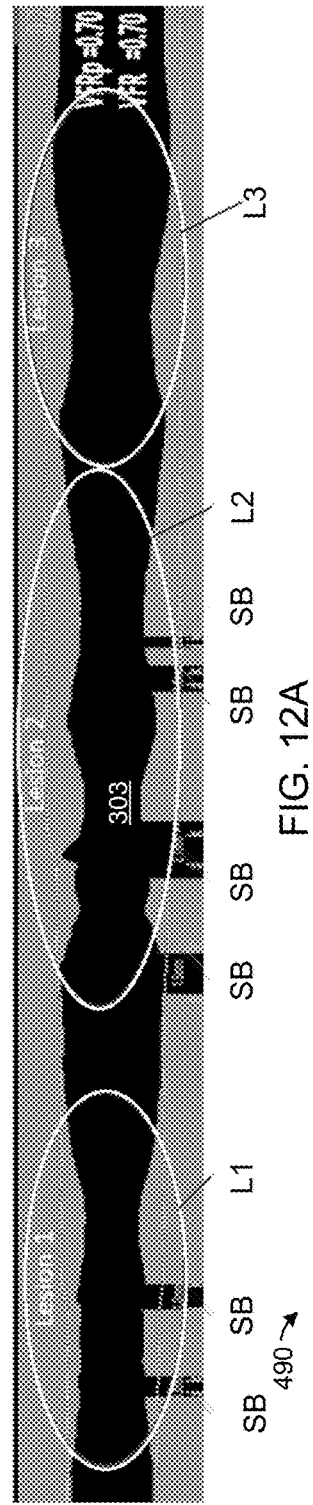
FIGS. 12A-12C depict additional vessel representation in the form of profile views of three lesions suitable for performing a clustering analysis to determine stent deployment options according to an illustrative embodiment of the invention.
Figure 12B:
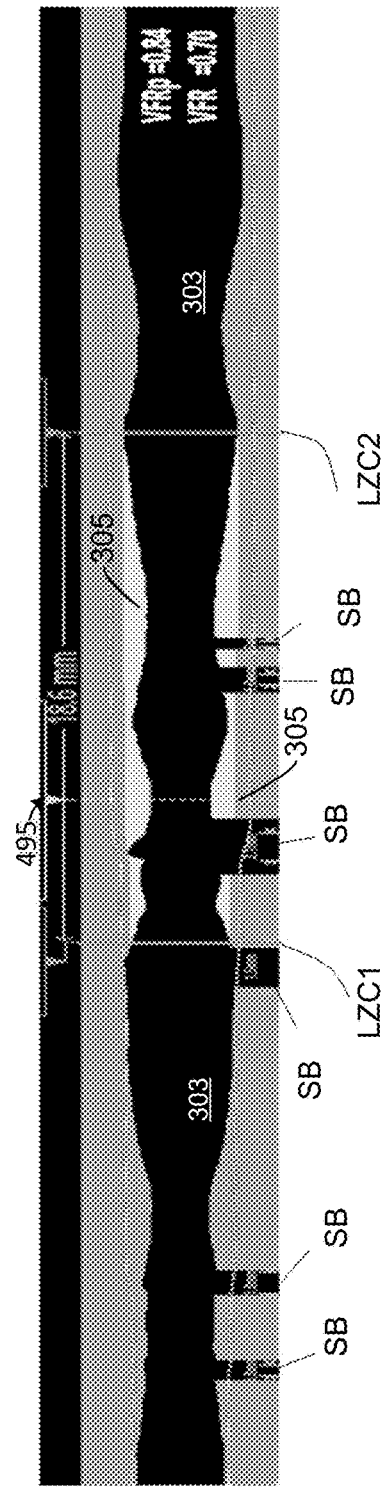
Figure 12C:
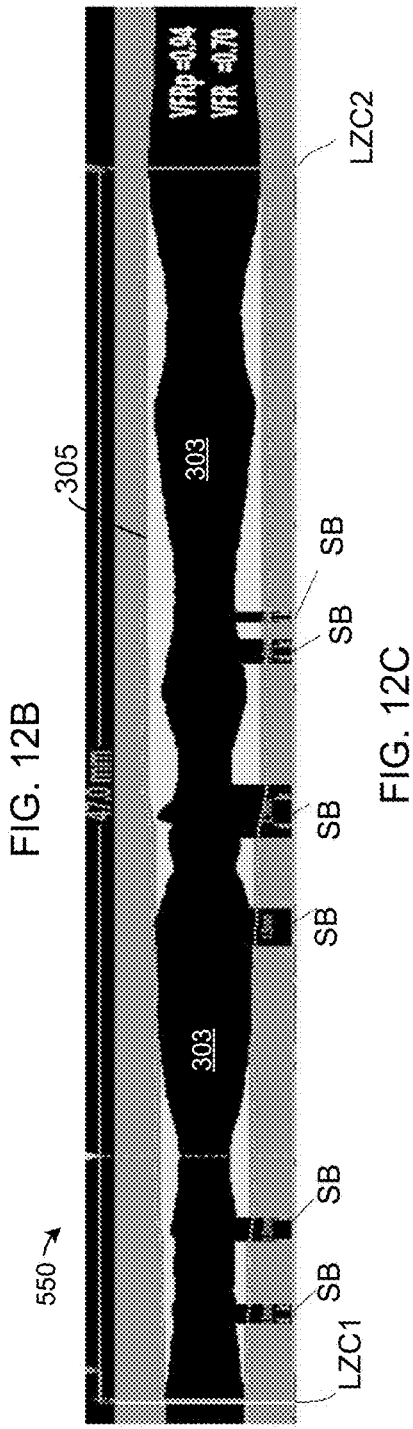

A cluster based analysis to identify and select regions of candidate stent overlap can be useful because such regions of overlap can be identified as regions in which some level of stenting is required to satisfy the constraints of the stent planning software given the presence of flow obstructing stenosis, lesions, bottlenecks, etc. FIG. 7 shows an exemplary plot of clusters C1, C2, and C3 relative to post stent VFR and the ration of the stent length to length of pullback through the blood vessel. Each cluster C1, C2, and C3 corresponds to a stenotic lesion as shown in the longitudinal views of FIGS. 8A-11. FIGS. 12A, 12B and 12C also show profile views generated with blood vessel data for three lesions that can be used to perform a clustering analysis. As shown, in the foregoing figures the clusters and lesions map to and correlate with each other.

In general, a clustering analysis is used to guide the stent placement by identifying the critical sections that need to be stented first. A plot of the VFRpost vs length of stent normalized to the pullback length for each candidate stent shows distinct clusters as shown in FIG. 7. There are three clusters that can be seen and the number of clusters correlate with the number of lesions in the pullback. Based on the cluster analysis the following stenting guide is derived, a default stent is shown at the critical stent section as shown in FIGS. 12B and 12C to achieve the increase in VFR. Although VFR is referenced, the clustering analysis applies to any parameter described herein. FIGS. 8A-11 depict additional representations of a blood vessel with lumen 303 and various landing zone positions LZ1 and LZ2. These figures show regions of overlap for which stent placement for different landing zones advantageously changes VFR. These overlapping regions can be analyzed using a cluster-based approach as discussed herein. The position of the landing zone selected by an end user or determined using methods and systems disclosed herein change the lumen profile and expands regions of stenosis 305.

Figure 8F:
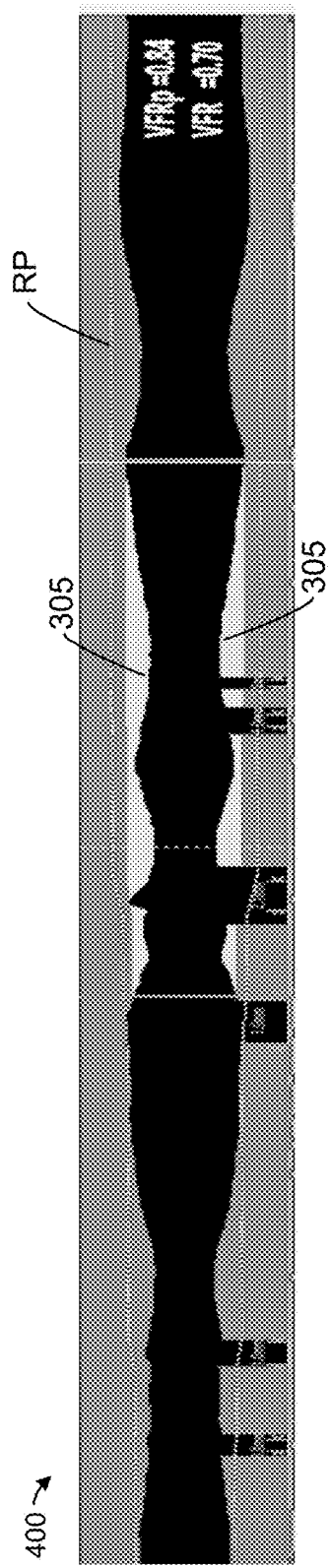
FIG. 8F is a lumen profile view corresponding to a vessel representation showing the overlapping regions of cluster 1 from FIG. 7 and FIGS. 8A-8E.
Figure 8G:
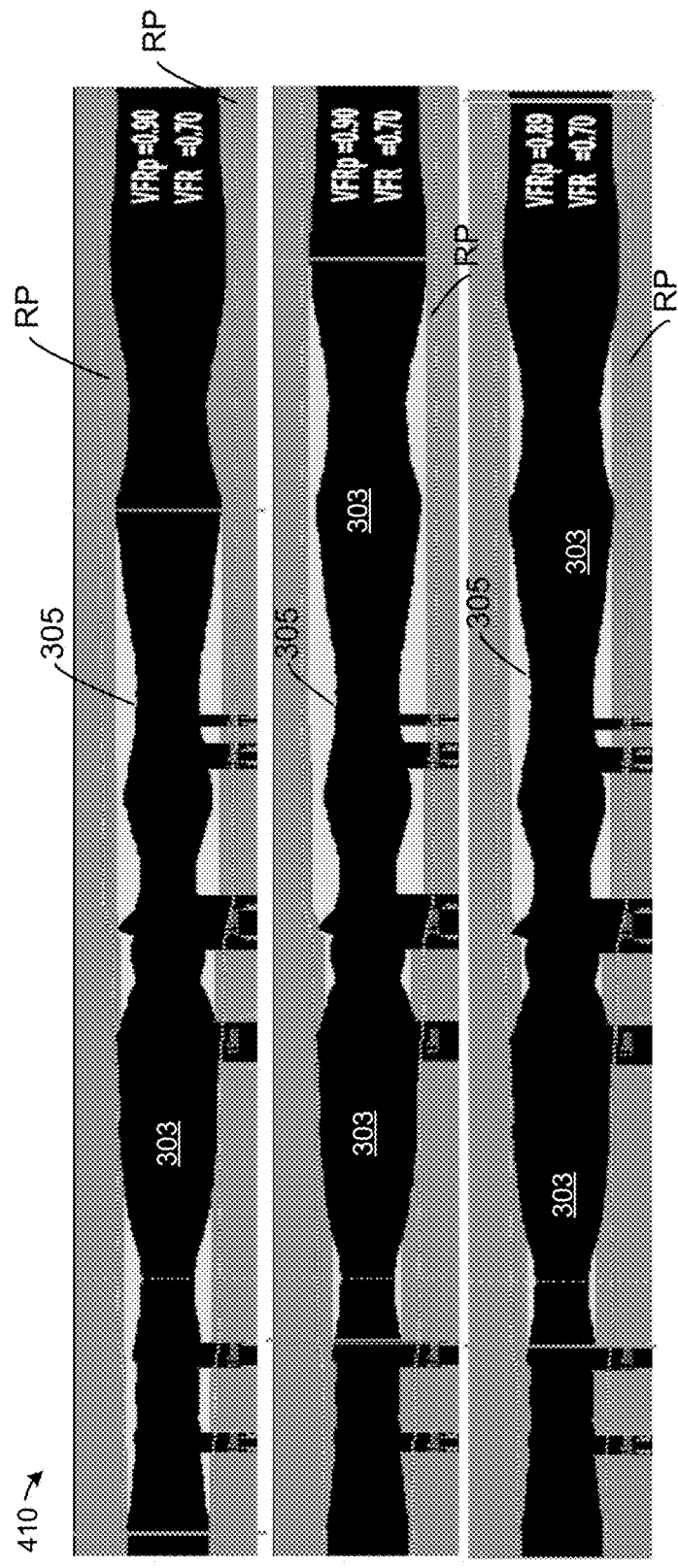
FIG. 8G depicts additional user interface views showing blood vessel representations including longitudinal representation of stenosis of cluster 2 of FIG. 7 according to an illustrative embodiment of the invention.
Figure 9:
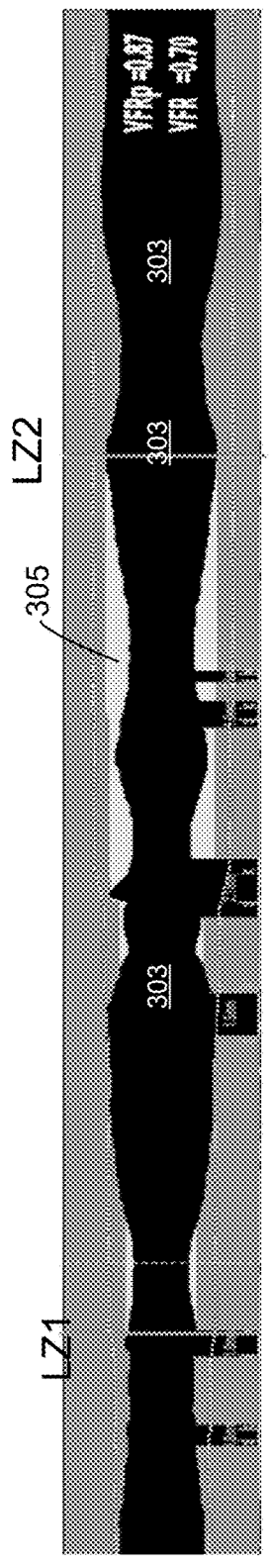
FIG. 9 is a lumen profile view corresponding to a vessel representation showing the overlapping regions of cluster 2 from FIG. 7 and FIG. 8G according to an illustrative embodiment of the invention.
Figure 10:
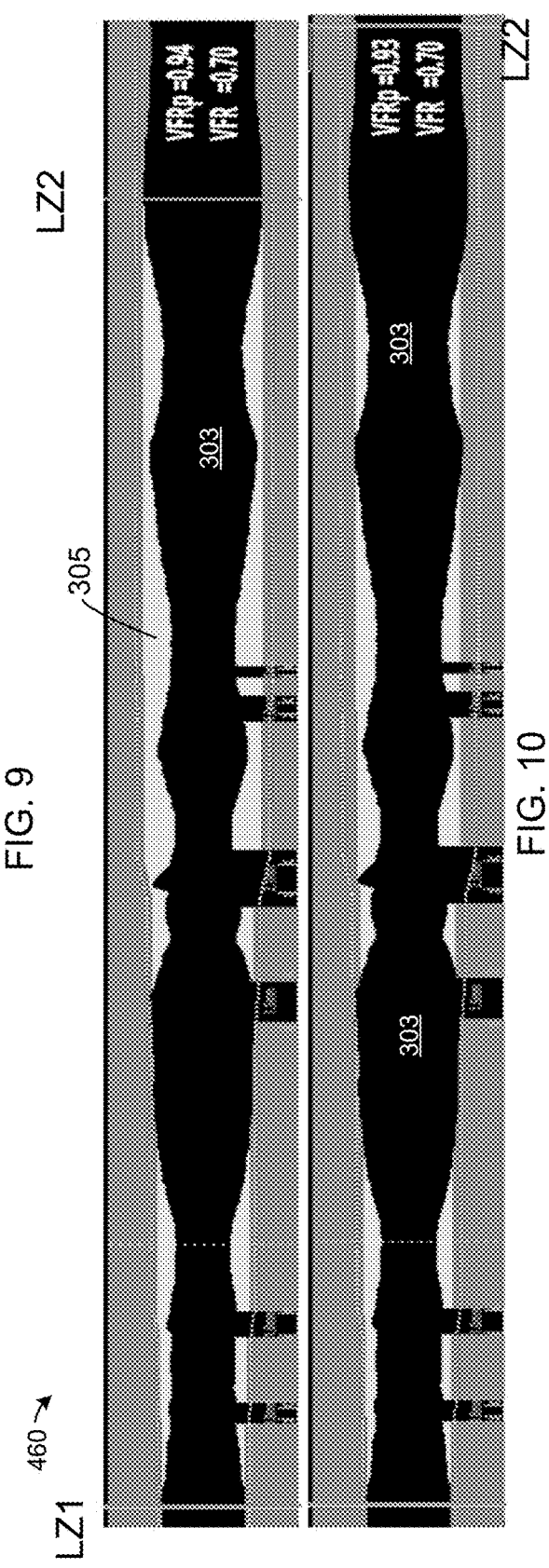
FIG. 10 depicts additional user interface views showing blood vessel representations including longitudinal representation of stenosis of cluster 3 of FIG. 7 according to an illustrative embodiment of the invention.

Further, FIGS. 8A-8E show vessel representations in the form of a vessel or lumen profile representation or view. FIGS. 8A-8E correspond to cluster 1 in FIG. 7. The overlap region for cluster 1 is shown in FIG. 8F. In FIG. 8F, profile view/vessel representation 400 shows the overlap region is 18 mm in length and is in between the two vertical lines that bound a region where stenting should occur. The vertical line pairs in each of FIG. 8A-8E correspond to the five points shown for cluster 1 in FIG. 7. FIG. 8G shows three profile views that correspond to cluster 2 in FIG. 7. The three points in cluster 2 map to the three regions demarked as between each of the three landing zone pairs LZ1, LZ2 of FIG. 8G. FIG. 9 shows the overlapping region in cluster 2, which is 30 mm in length. In FIG. 7 the overlapping region can be shown by circling a point in the cluster as shown in one embodiment. FIG. 10 shows two profile views 460 that correspond to cluster 3 in FIG. 7. FIG. 11 is profile view 470 shows the overlapping region in cluster 3, which is 47 mm in length. Areas of overlap based on clustering are recommended for stent landing zone positions in one embodiment.

Figure 2A:
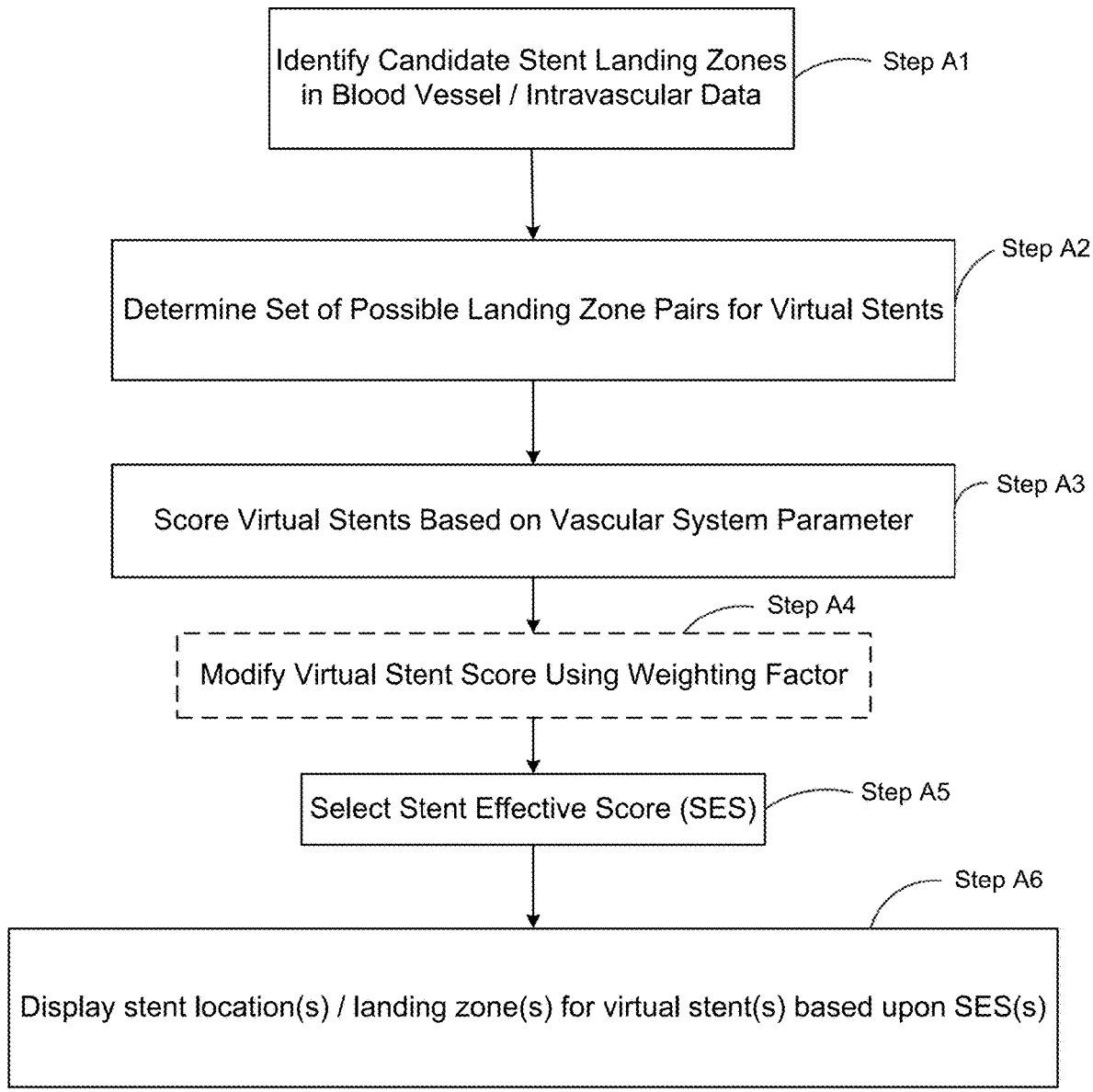
FIGS. 2A, 2B and 2C are flow diagrams of stent planning methods that use blood vessel data from in vivo data collection during a pullback in accordance with an illustrative embodiment the disclosure.
Figure 2B:
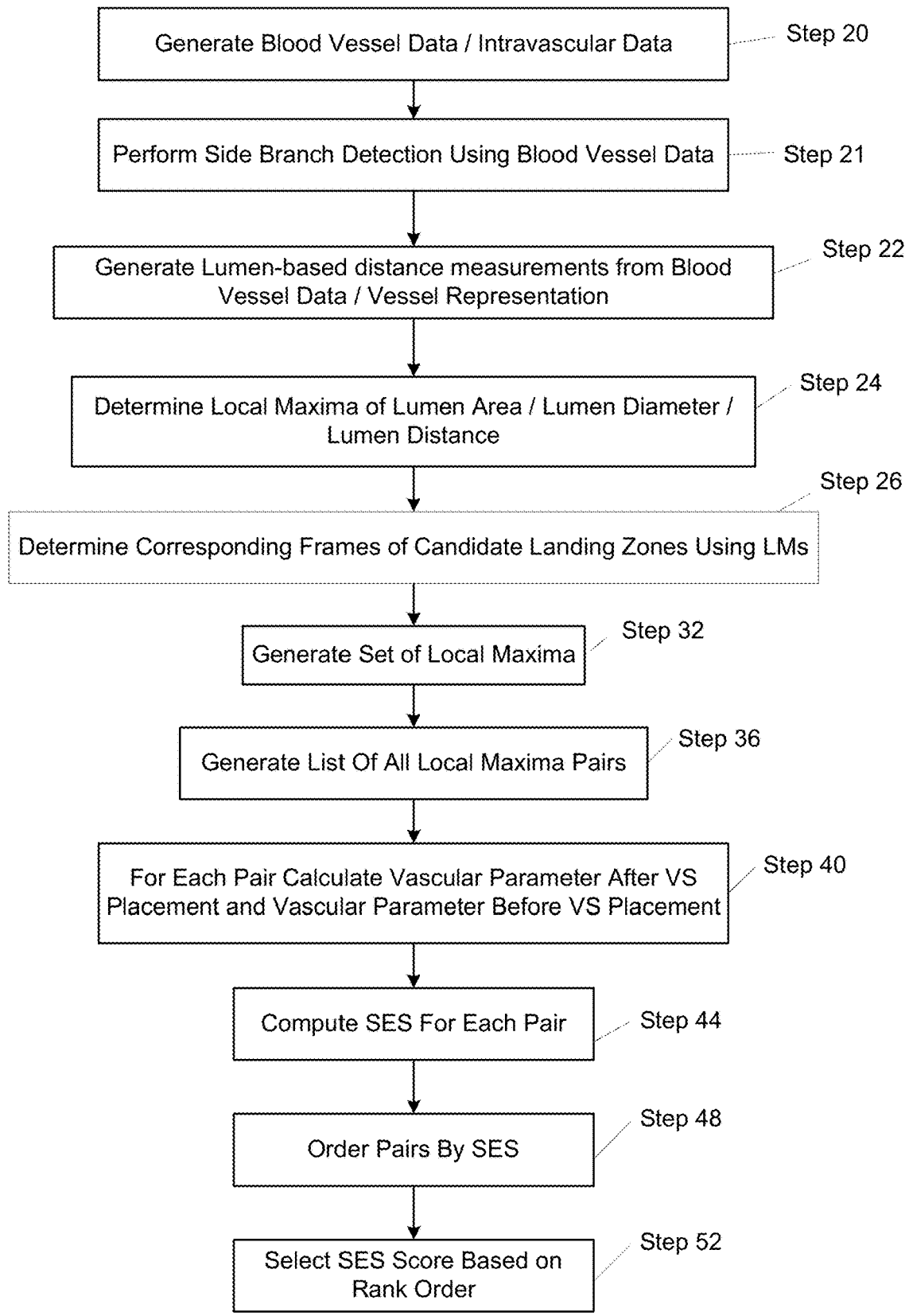
Figure 2C:
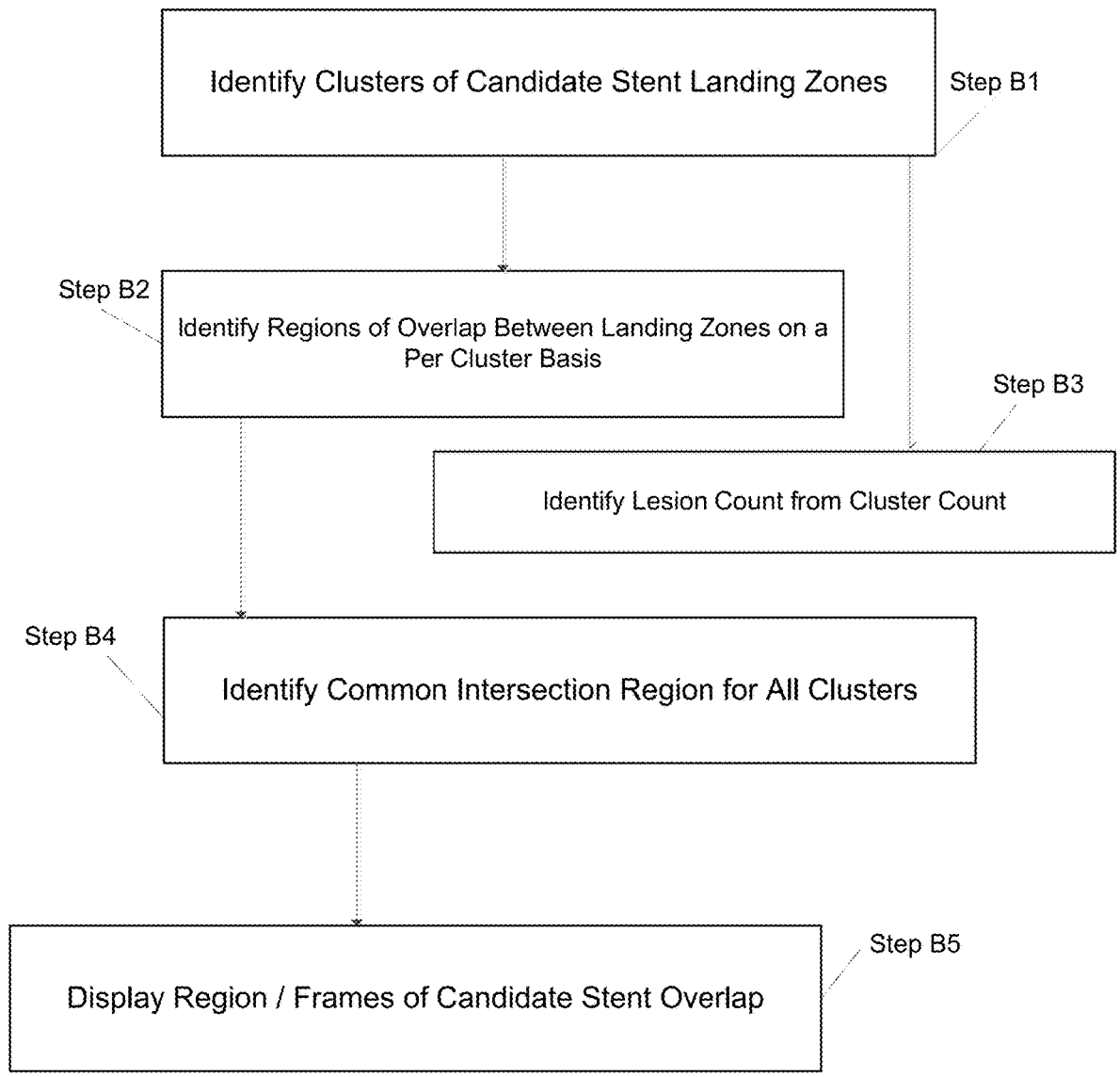

FIG. 2C describes the method steps of an exemplary clustering analysis approach. In general, the 12A, 12B and 12C. Based on the cluster analysis a stenting guide is derived. For example, landing zones or a default stent can be shown at the critical stent section in the user interface. Regions of overlap for multiple clusters can be used to generate this section and its landing zone endpoints. This is the stent that the software places automatically when stent planning is enabled, in one embodiment, as shown in FIG. 12B. The critical section corresponds to the intersection or overlapping region that is common to all three clusters. Using the cluster analysis an area where the end user should consider evaluating stent deployment is shown.

FIG. 12A shows the clusters near side branches SB and lesion L1, L2, and L3. The lumen 303 is in the middle of the image. The three lesions are in tandem from left to right and are candidates for a cluster analysis. In FIG. 12B, the critical landing zones, LZC1 and LZC2, based on cluster intersection/overlap, these landing zones are good candidates for stent deployment. With regard to each cluster, C3 gives biggest incremental improvement for stenting. The critical stenting zone does appear to be identify by the interrelationship of the clusters. Region 305 shows stenosis or lesion tissue that should be expanded with a stent to increase flow. Typically, the system would indicate not to ignore lesion C2 because overlap from cluster occurs there. In FIG. 12B, a vertical dotted line 495 and an associated bracket shows a section suitable for stent placement to change the VFR to 0.85 in response to this section being stented. If only this section is stent it is possible to increase the VFR from 0.70 to a predicted value of 0.84.

In general, a clustering analysis is used to guide the stent placement by identifying the critical sections that need to be stented first. A plot of the VFRpost vs Length of stent normalized to the pullback length for each candidate stent shows distinct clusters as shown in FIG. 7. There are three clusters that can be seen and the number of clusters correlate with the number of lesions in the pullback. Based on the cluster analysis the following stenting guide is derived, a default stent is shown at the critical stent section as shown in FIGS. 12B and 12C to achieve the increase in VFR. Although VFR is referenced, the clustering analysis applies to any parameter described herein or otherwise suitable for use with blood vessel imaging and stent deployment such as FFR.

Referring back to FIG. 3A, a reference profile can be created for the main vessel 106 and/or a reference profile 108 can be created. Additional details for reference profiles are described in U.S. patent application Ser. No. 14/115,527 entitled "METHOD AND APPARATUS FOR AUTO-MATED DETERMINATION OF A LUMEN CONTOUR OF A STENTED BLOOD VESSEL." Reference profiles are also shown that vary for different depictions of an artery with VFRp (VFR post morphing of lumen and vessel after application of a virtual stent) and VFR (VFR determined before deployment of identified and SES scored virtual stent). See FIGS. 8A-8B, for example. Using the reference profile (dotted line) 108 also referred to as RP, an estimated blood vessel diameter can be calculated by using distal and proximal reference profile diameters. The proximal and distal reference can be analyzed using a power law relationship.

In one embodiment, the power law is given by the expression:

$$D_b^\varepsilon(i) = D^\varepsilon(i+1) - D^\varepsilon(i) \quad \text{(Eqn. 1)}$$

where $D(i+1)$ is the proximal reference profile diameter and $D(i)$ is the distal reference profile diameter; where $D_b(i)$ is the estimated true blood vessel diameter; and $\varepsilon$ is a power-law scaling exponent that has a value between 2.0 and 3.0 as determined empirically.

The difference between the estimated blood vessel diameter and the actual blood vessel diameter detected by OCT imaging provides the level of blood vessel obstruction. In one embodiment, the level of blood vessel obstruction is given by the expression:

$$D_{obstruction}(i) = D_b(i) - D_{OCT}(i) \quad \text{(Eqn. 2)}$$

where $D_b(i)$ is the estimated true blood vessel diameter, and $D_{obstruction}(i) = D_b(i) - D_{OCT}(i)$ is the actual blood vessel diameter measured by OCT.

In an embodiment, a max diameter frames method is used to assess side branch obstruction. Instead of using a reference profile, the branch diameter is estimated using the maximum diameter in the main vessel segment distal and proximal to the current branch.

In an embodiment, a flow method is used to assess blood flow in an artery. For example, a flow method can be used to evaluate flow in artery that has been altered due to a stenosis, under inflated stent, narrowing or other obstruction in the artery. Using Virtual Flow Reserve (VFR) the flow going into each side branch can be estimated. The difference in flow down a given side branch due to the difference in OCT based branch diameter $\text{Flow}_{OCT}(i)$ and the true branch diameter $\text{Flow}_b(i)$ is an additional indication of the effect on flow due to the obstructed side branch. The true branch diameter can be calculated using one of the methods described above by either using the reference vessel profile or the max diameter frame in the distal and proximal segments. The flow method can be given as the following expression:

$$\text{Flow}_{obstruction}(i) = \text{Flow}_b(i) - \text{Flow}_{OCT}(i) \quad \text{(Eqn. 3)}$$

In various embodiments, a stenosis or other obstruction is represented on a user display using visual indicia, such as color-coding. The indicia can be coded to confer the level of obstruction. These indicia can also be set based upon user input via a user interface.

In complex lesions, the best optimal location and size of the stent is not always obvious. Several factors like flow, branching pattern, vessel diameter, etc. need to be taken into account. The systems and methods described herein that use diagnostic intravascular imaging systems and algorithms designed to operate on such system outputs to determine the optimum location and size of the stent. An end user, such as a cardiologist, researcher or technician can use the algorithm generated virtual stent as a guide to place the stent. There can be instances where the clinician or other end user cannot predict which size stent and at what location would give the best outcome for the patient in terms of improved blood flow and reduced restenosis. In one embodiment, the systems and methods of the disclosure are implemented using computer algorithms to predict a desirable location for placing the stent that maximizes desirable quantities such as blood flow for the shortest possible stent length.

As part of this process, in one embodiment, the method operates on the intravascular data collected in vivo with a data collection probe to identify all possible frames that are candidate landing zones for a stent. All combination pairs of these landing zones are computed, with each pair corresponding to a virtual stent's distal and proximal landing zone. An optimization step is performed where a ranking or score is provided to each virtual stent based on the improvement in flow and the length of the stent. This provides a general overview of one implementation of a stent planning process.

In one embodiment, as part of stent deployment planning, the candidate virtual stent (also referred to as a stent representation) is one that maximizes flow per length of stent and is in the optimal landing zone. In general, the "best" or otherwise highly ranked candidate virtual stents are those that maximize, improve upon or otherwise change one or more intravascular parameters in a desirable way.

In one embodiment, as shown in FIG. 2A, a method of stent planning is depicted. In general, identifying local maximum based on area or diameter (as a correlated factor with area), results in the selection of areas for landing zones such that there will not be tearing, tenting or any sharp discontinuities as a result of the stent width, the stent expansion, and the regions of the vessel that acts as the landing zone. Accordingly, large diameters regions in the artery are the candidate landing zones the methods described herein are designed to target while regions of the artery with side branches, high taper, narrowed regions, and others are avoided. This consideration informs the steps of the method of FIG. 2A and others described herein. In one embodiment, the method includes storing, in an electronic memory device, intravascular data of a blood vessel generated using an intravascular probe pulled back through the blood vessel.

As shown in FIG. 2A, the method includes identifying candidate sent landing zones in intravascular data (Step A1). The method also includes determining a set of possible landing zone pairs (Step A2). Scoring virtual stent landing zones based on changes to one or more vascular system parameters (Step A3) is another step. Optionally, it is possible to modify the score using weighting factors such as described herein (Step A4). In one embodiment, the changes are between stented and unstented state of a blood vessel such as VFR pre- and post-virtual stent deployment. The method can include ranking and selecting a SES (Step A5) and the associated landing zones with selected score. Also, the method can include displaying landing zones for a virtual stent having a selected score (Step A6).

It is worth noting that the disclosure is not limited to maximal values and all of the values described herein can be also evaluated in terms of a set threshold or comparison to a baseline to determine some degree of improvement in the parameter as a result of the position and length of one or more stents. In one embodiment, as part of one of various possible work flow scenarios for an end user, the virtual stent is presented to the end user as a default virtual stent as part of the graphical user interface of the intravascular data collection system.

In one embodiment, the systems and methods disclosed herein automate the decision process of placing a stent at a location, having a proximal location and a distal location, such that the stent is deployed between the proximal location and the distal location such that one or more dimensions of the stent, such as length and diameter, are selected to improve blood flow. The improvement to blood flow can be within a range of values, an optimal flow value, a relative extremum flow value, or another flow value selected by an end user via a user interface or other input mechanism. In one embodiment, the algorithm searches through all possible combinations of stents to evaluate the best stent location and size.

In this way, the systems and methods described herein can identify candidate stents with a recommended size, length, and placement location that is likely to result in a desirable outcome for the patient in terms of the criteria selected for scoring the candidate virtual stents such as for example parameters that change after stent deploy to improve blood flow and/or otherwise reduced restenosis. The disclosure also incorporates by reference in its entirety U.S. patent publication 20110071404 "Lumen Morphology and Vascular Resistance Measurements Data Collection Systems, Apparatus and Methods" filed on Sep. 22, 2010 which described identifying and displaying lumen contours as well described methods of automatically constructing a mean-diameter profile of a branched vessel via automated processing of intravascular images. The use of mean diameters and lumen areas can be used to identify local maxima and thus identify candidate landing zones as described herein.

In brief overview, once the image of a portion of a coronary vessel of interest has been acquired and analyzed, the system calculates the optimal sizes and locations for stent placement. The term "locations" means the positions in the vessel at which the ends of the stent make contact with the vessel walls. These locations may be referred to as landing zones or sites.

In operation, the stent placement algorithm first identifies all possible frames that are candidates for placement locations or landing zones for a stent. Landing zones for each end of the stent are computed for all combination pairs of distal and proximal locations in the vessel, with each pair corresponding to a stent's distal and proximal landing zone respectively. An optimization step then may be performed to rank or score each potential stent placement pairs based on the calculated improvement in flow and the total length of the stent. In one embodiment, the desirable or optimal stent to deploy is one which maximizes flow per unit length of stent and is in the optimal landing zone. This potential stent is presented to the clinician or other end user as the default potential stent in one embodiment. These tools can be used with angiography to further enhance stent delivery.

In more detail and referring to FIG. 2B, another exemplary stent planning or candidate virtual stent placement method is shown. Initially, blood vessel data such as imaging data, distance measurements relative to blood vessel, intravascular data, angiography data, tomography data or other data is generated that is suitable to generate a representation of a blood vessel for user review and display on a diagnostic system (Step 20). In one embodiment, side branch detection is first performed (Step 21) using such a representation. The method is then able to ignore the detected side branch locations to determine lumen diameters, lumen radii, lumen chords, lumen areas, or a representation thereof such as a lumen area curve (Step 22) using one or more methods such as those described in U.S. patent application Ser. No. 14/115,527 entitled "METHOD AND APPARATUS FOR AUTOMATED DETERMINATION OF A LUMEN CONTOUR OF A STENTED BLOOD VESSEL." In general, this step includes generating lumen-based distance measurements from blood vessel data and/or the vessel representation. (Step 22)

In general, a lumen area curve or a lumen diameter curve is a representation of lumen areas or diameters generated based on a representation of blood vessel created using data from an intravascular pullback such as an OCT or IVUS representation of a blood vessel. The local maxima corresponding to areas of the blood vessel with a lumen that is sufficiently wide that it can be fit with a stent of a suitable thickness are identified. This can be performed using a curve or a table by which lumen areas along the length of the vessel or lumen diameters (which are directly correlated with lumen areas) are ranked, searched, sorted or otherwise evaluated and compared to identify local maximum values. The method can use a lumen area curve or other data sources to generate blood vessel data such as intravascular data. This data can come form other imaging modalities such as angiography, tomography and ultrasound. Local maxima (LM) can be determined from various types of blood vessel data such as intravascular data generated with an imaging probe (Step 24).

The stent placement method determines the frames corresponding to local maxima (LM) in the curve or generally from blood vessel data (Step 26). The local maxima (LM) values correspond to a cross-section of the blood vessel having a lumen diameter and thus a lumen area that is larger relative to other cross-sections of the lumen within a certain segment of the blood vessel. As a result, the image frames, formed from a plurality of scan lines, each correspond to a polar slice of the blood vessel. The frames with LMs define a set from which candidate virtual stent landing zones (LZ) can be identified. In partial, by using a selection process that generates a search window defined by the lengths of possible stents, such a window can be positioned relative to candidate landing zones to identify landing zone pairs where a virtual stent can be displayed in a representation of the blood vessel using a window size that corresponds to the stent length.

Figure 4A:
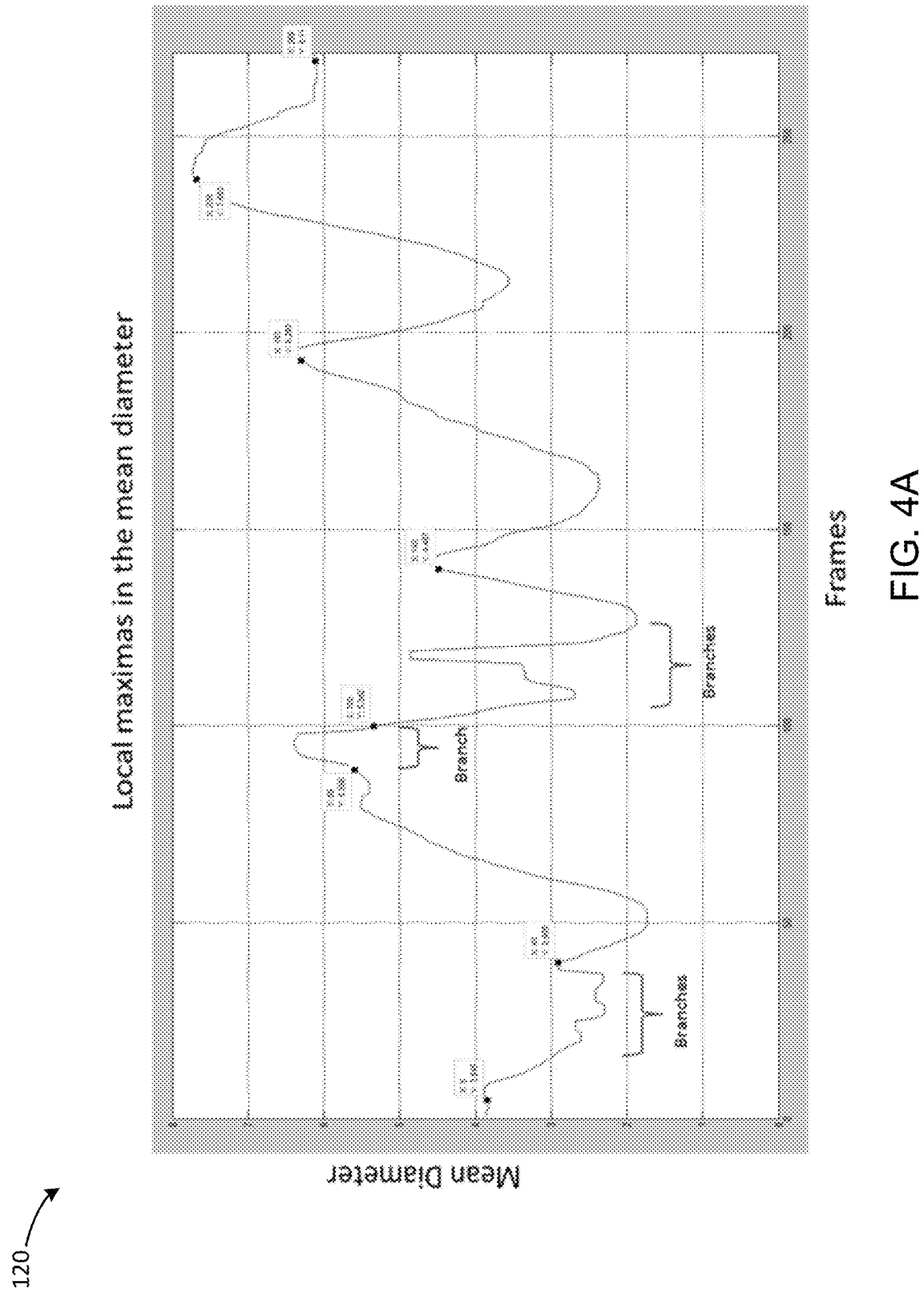
FIG. 4A is a graph displaying frame position plotted against mean lumen diameter for a region of coronary artery imaged using data from a pullback in order to show points corresponding to local maxima of vessel diameter in accordance with an illustrative embodiment the disclosure.
Figure 4B:
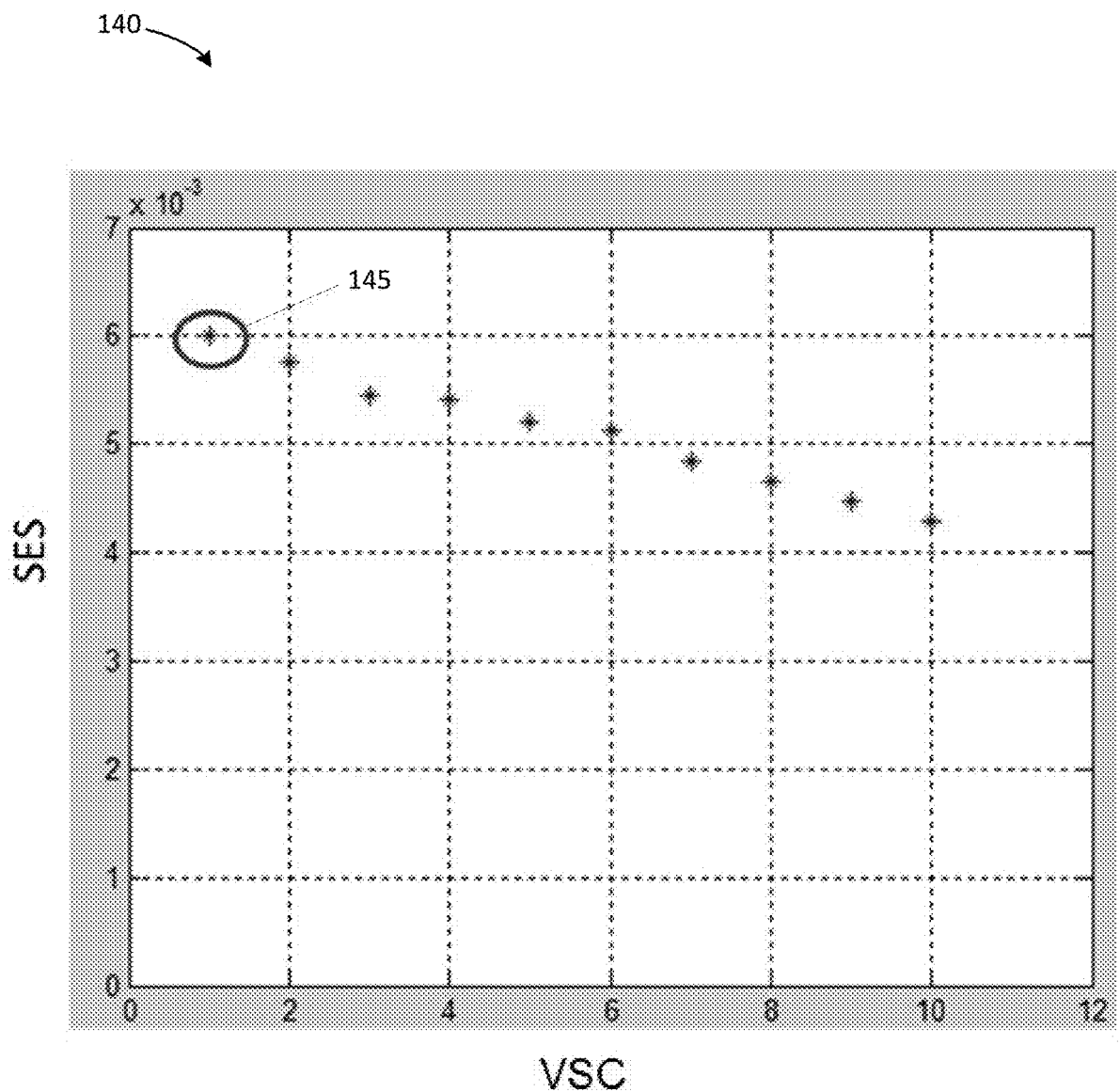
FIG. 4B is a plot of virtual/hypothetical stent candidates (VSC) plotted versus stent effectiveness score (SES) values in accordance with an illustrative embodiment the disclosure.
Figure 5A:
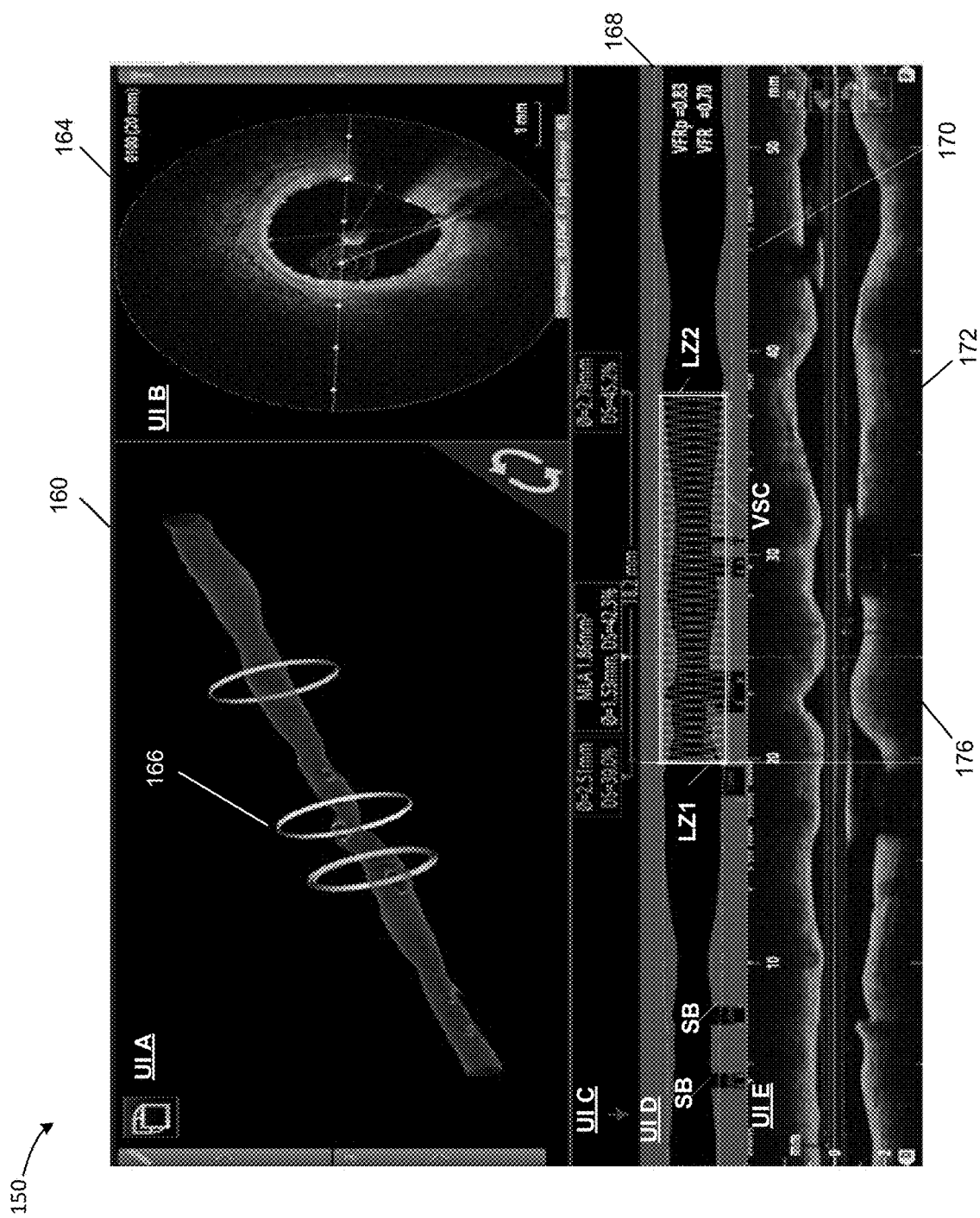
FIG. 5A is an embodiment of a user interface display of a stent planning/placement system with a VSC shown relative the landing zone frames in accordance with an illustrative embodiment of the disclosure.
Figure 5B:
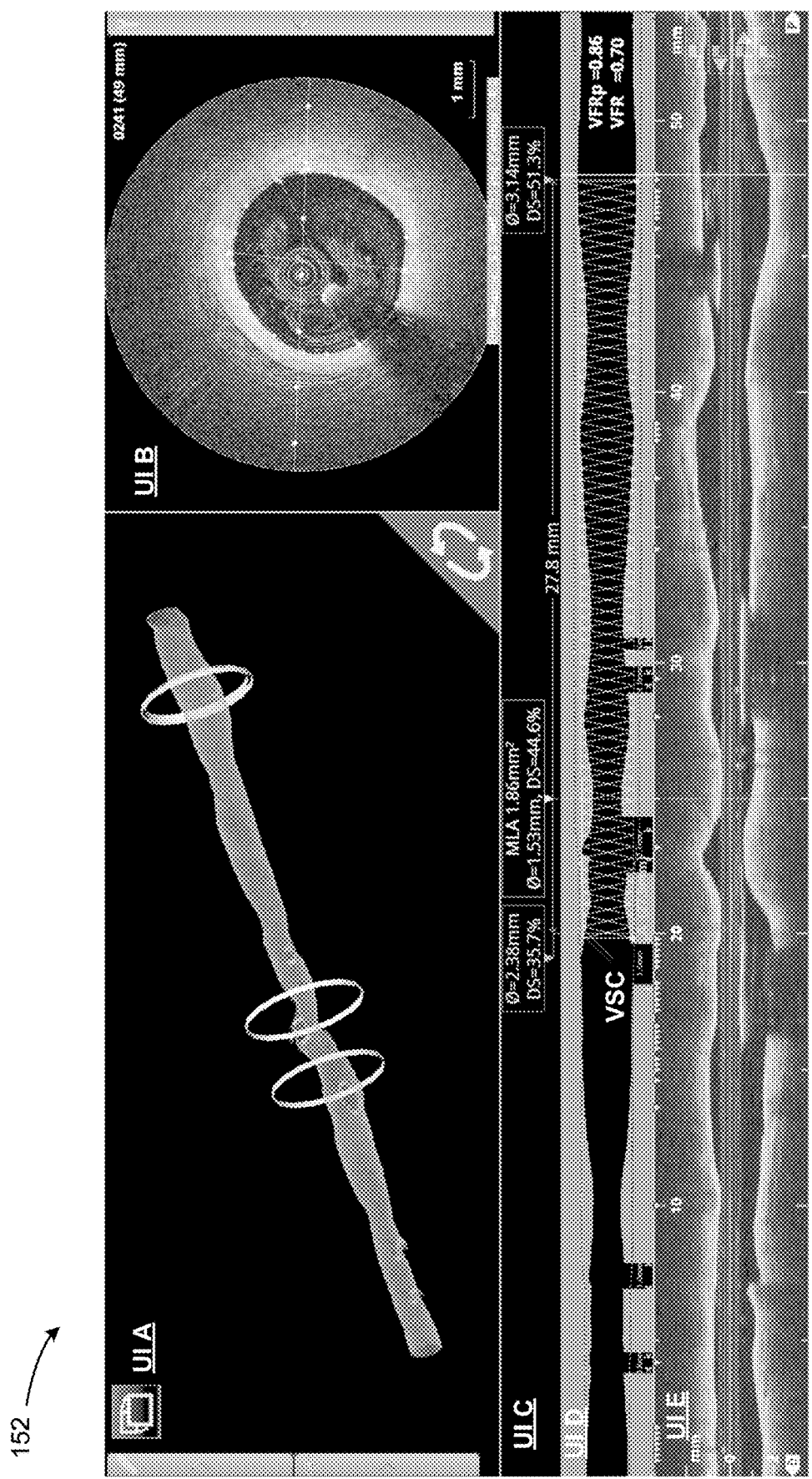
FIG. 5B is another view of the user interface of FIG. 5A in accordance with an illustrative embodiment of the disclosure.
Figure 6:
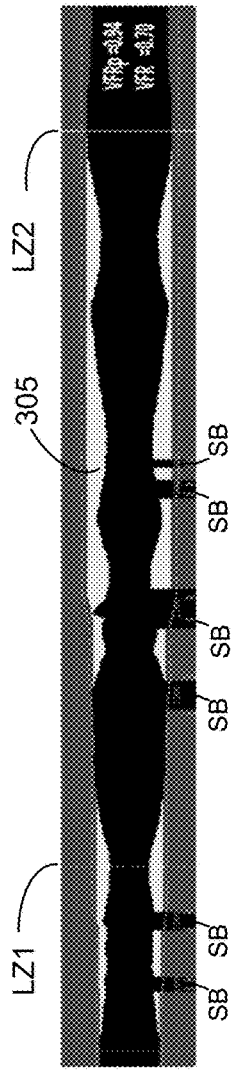
FIG. 6 depicts a longitudinal view of a blood vessel representation generated using intravascular in vivo data that shows landing zones and areas of the vessel wall that are obstructing flow and candidates for displacement by stent deployment at the landing zones shown.

FIG. 4A shows a plot 120 of mean diameter (y-axis) versus frame number (x-axis) for a set of blood vessel data. Each frame is a slice of the blood vessel or image representation thereof in one embodiment. The local maximums in the mean diameter are show as dark points along the curve. Side branch locations are also shown. This set of local maxima provides one representation of lumen area/lumen diameter data to identify candidate landing zones. FIG. 4B is plot 140 of virtual/hypothetical stent candidates (VSC) plotted versus stent effectiveness score (SES) values. As shown, by the series of points that slope down to the right, the virtual stent frames or landing zones are ranked with landing zone 145 being the highest in rank order and possibly the preferred candidate as a location for stent deployment. All of the local maxima candidate frames shown in FIG. 4B are candidates for stent deployment. The selection of stent length further constrains these values to a pair of frames in one embodiment. In one embodiment, VSC are depicted as hatched pattern on a panel or subscreen of a user interface as shown in FIGS. 5A and 5B.

The stent lengths to be devalued can be specified by an end user via a user interface input. In one embodiment, the window is set as the shortest stent length available from the set of stent that the end user can use for a given procedure. In one embodiment, the stent length is about 8 mm. However, stent lengths can be set as a search window for landing zones without limitation. In addition, two stents can be used with the window set based on their combined length. The stent placement algorithm next generates a set or list (Step 32 of FIG. 2) of the local maxima.

The system next (Step 36) generates a list of all combinations of LM pairs. Each pair includes two possible stent landing zone locations, one for each end of the stent. There is a total of $$Nstents1 = \binom{N}{2}$$

or "N taken 2 at a time" pairs of stent landing zone location candidates, where N is the number of local maxima. This binomial coefficient representation is used because there are n ways to choose 2 elements, disregarding their order, from a set of N elements. The binomial coefficient is the number of ways of picking unordered outcomes from possibilities, also known as a combination or combinatorial number. The method uses such an approach to pick frames as candidate landing zones (LZ) based on local maximum of lumen area/lumen diameter. This follow because a stent is advantageous placed in a region of the lumen where the ends of the stent fit with the lumen profile and avoid a step or other sharp discontinuity when deploying the stent.

For example, if there are three local maxima A, B, C, then $$Nstents1 = \binom{3}{2} = 3$$

and the three candidates are (NAB, NBC and NAC). Thus, the landing zone frame pairs would be pairs of frames A and B, pairs of frames B and C and pairs of frames A and C.

From these local maxima candidates a further combination is generated (Step 40) where $$Nstents2 = \binom{Nstents1}{2}.$$

Again, because Nstents1=3 then Nstents2=3 which is every possible combination of two stents in a given pullback. As discussed herein, it may sometimes be advantageous to deploy two shorter stents rather than one longer stent. The total stent length or the window used for searching for landing zones would be the length of each stent together.

For each stent landing zone combination, which defines one or more virtual or hypothetical stents for deployment in the blood vessel, the system next generates (Step 44) a stent effectiveness score (SES). The SES takes into account the flow improvement as estimated using the change in Virtual Flow Reserve that results from the placement of the stent of a given diameter and the length at a specific location in the vessel. The stent effectiveness score is defined as:

SES=ΔVFR/(Stent Length)=(VFR$_{after\ placement}$−VFR$_{before\ placement}$)/(Stent Length)

where ΔVFR is the change in the VFR number that results from the placement of that stent.

The denominator is designed such that stents that are short and provide the maximum improvement in VFR, will have higher SES values. That is, the shorter of two stents producing the same ΔVFR will have a higher SES because a shorter stent is preferred over a longer stent as discussed herein. In general, a shorter stent can more easily track the contours of an artery. Accordingly, two shorter stents can more closely follow the contours of an artery and bend. A longer stent, the length of two smaller stents cannot bend in the same way at a point of flexion. As a result, one aspect of the disclosure relates to selecting multiple shorter stents by assigning them a higher SES score in various embodiments.

The SES can be further modified by including additional weighting factors. The weighting factors can be a penalty factor that reduces a given SES value or an additive factor that increases a given SES for a particular stent deployment scenario or set of criteria. The additive or penalty factor can be used to generate terms weighted based on some of the factors outlined below and as otherwise described herein.

The quality of landing zone, which in various embodiments is determined by tissue characterization or by the difference between the normal vessel area and the actual lumen area in that region can be used as a factor. This can be facilitated by using a calcium detection software module or a tissue characterization software module.

The total lumen area of all branches that are covered by the stent can be used as a factor. If a small side branch is jailed, this may be a small negative factor, but if all or a majority of branches are jailed, this would result in a large negative factor to reduce a given SES as applicable. In this way, jailing of stents during stent deployment can be avoided or at least presented to an end user.

As part of the stent planning tools, an end user can set stent limits based on user preferences such as BRS, thickness, length, material, and other factors. These inputs can be used to adjust the SES weighting factors based on criteria relating to how such user selections affect the benefits of a particular landing zone.

The amount of tapering in artery can affect the SES for particular types of stents. In some embodiments, a tapered artery or a tapered region of an artery is not suitable for use with a BRS. As a result, the presence of a taper, such as detected by the geometry of the lumen contours can penalize or decrease the SES score for the use of such a stent in an artery having a tapered region or other geometric constraint ill-suited for deploying a BRS. For some BRS, the ability to expand the stent can be constrained such that using it in the vicinity of a vessel region with too much taper—such as a steep cone-shaped region is not desirable. Thus, a landing zone frame with such a taper would have its SES reduced by a negative weighting factor if a BRS stent type was identified in the user interface. Thus, the expansion limit is on stent constrains used in certain locations with a significant taper and is the basis for SES reduction.

In addition, physiological constraints relating to the type, size, thickness and other factors by which a stent is selected for a given artery can be used as the basis for an additive weighting factor or a negative weighting factor when determining SES for a given artery type and landing zone scoring. Accordingly, the weight factor used for SES computation can vary based on artery type such as for example carotid artery, right coronary artery, left coronary artery, circumflex artery and the left anterior descending, and other arteries as applicable.

After the SES is computed for each pair of local maxima, the placement algorithm orders (Step 48) the pairs and selects the best SES. The highest scoring stent locations are then displayed (Step 52) as the best corresponding stent location(s). The details described herein with regard to FIG. 2B can also be used with regard to the other methods and processing steps described in FIG. 2A and otherwise.

In another embodiment, the user may set a target VFR (or other parameter) or minimum VFR (or other parameter) that the user would like to achieve and the stent placement algorithm searches for the stent location combination that provides the highest SES with a predicted VFR (or other parameter) above or equal to the physician set target VFR (or other parameter). Various VFR values and predicted or post-stenting VFRp values are depicted in the longitudinal representations of the blood vessel segments shown herein. Similarly, this same parameter target setting can be performed using the user interface and any of the cardiovascular parameters described herein.

Other parameters that the end user can set or that can be used in lieu of or in addition to VFR to assess based on landing zones and SES values include, without limitation, flow velocity, a pressure value, a maximum flow, a minimum flow, one or more fractional flow reserve (FFR) values, virtual fractional flow reserve values, coronary flow reserve (CFR) values, coronary flow velocity reserve (CFVR) values, instantaneous flow reserve (IFR) values, one or more index of myocardial resistance (IMR) values and a vascular resistance value, a combination of the foregoing, a weighted average of one or more of the foregoing and another value, and values derived from the foregoing FIGS. 5A and 5B depicts a typical user interface screens, 150, 152, respectively of a display that is connected to an intravascular diagnostic system such as that described with regard to FIG. 1. With respect to interface screens 150, 152, various other user interface components of the diagnostic systems and software-based tools UIA, UIB, UIC, UID, and UIE are shown. The user interface is used by an end user for stent planning using the systems and methods described herein. As part of the operation of the system, one or more user interface software modules are executed to display information to a user regarding the processed intravascular data. This display is composed of five r screens. The first user interface screen 160 (UIA) is a perspective view of an OCT image of a vessel of interest. The second user interface screen 164 (UIB) is an axial cross-sectional view of a portion of the vessel indicated by ring 166 in user interface screen 160. As shown in FIG. 5B, the VFR without the VSC depicted is 0.7 and it increases to a predicted value of VFRp of 0.86 if the VSC shown were depicted.

By moving the ring with the user interface, different cross-sections may be shown in user interface screen 164. User interface screen 168 (UID) is a stylized longitudinal cross-section of the vessel on user interface screen 160. User interface screen (UIC) shows details of measured and/or determined values for the vessel representation in user interface screen 168 (UID). A stent has been located on the longitudinal cross-section so that the physician can determine fit. The black vertical bands are the branches of the vessel. User interface screen four is an image of an actual longitudinal cross-section of the vessel in user interface screen 160. Line 176 on both screens 168 and 172 also corresponds to the location of ring 166 on user interface screen 160. The VSC shown in interface screen 168 is user adjustable or determined based on determination of landing zones LZ1 and LZ2.

In one embodiment, an optimized search is performed that maximizes one or more variables that influence a stent deployment decision and stent placement. In one embodiment, such an optimized search-based approach treats each variable and/or the weight associated with such a variable as a dimension in a n-dimension space. In turn, the peaks in the resulting n-dimension space represent the stent that optimizes one or more (or all) of the variables specified.

In still another embodiment, a machine learning algorithm is trained based upon current physician practices for deploying stents. The training can be implemented by teaching the algorithm the weightings provided based upon one or more criteria variables that influence a stent deployment decision and stent placement. The algorithm training can also include different types of patient data and different types of arteries. Accordingly, using the trained feature set, the algorithm can predict a suitable location for a stent when presented with a new representation of an unstented vessel generated using intravascular data.

FIGS. 12A, 12B, and 12C show an exemplary user interface for stent planning and diagnostic analysis that depicts a representation of a blood vessel. In FIG. 12C, a user interface 550 showing two landing zones separated by 47.0 mm of the blood vessel with the lumen 303 and various side branches SB. the LZ associated with cluster 1 (LZC1) and the LZ associated with cluster 2 (LZC2) are shown. The three corresponding lesions can be stented to increase the VFR from 0.70 to the predictive VFR of 0.94.

With respect to the optimized search approach, the machine learning approach and others described herein, the variables can include any of the cardiovascular parameters described herein and other parameters including without limitation: landing zone quality (based on proximity to a side branch, tissue characterization, or other factors), total area of side branches jailed as a result of placement of one or more stents, amount of tapering present at a candidate landing zone location, user preferences specified as constraints through the user interface; and positional locations based on artery type (such as carotid artery, right coronary artery, left coronary artery, circumflex artery and the left anterior descending, and other arteries as applicable) and Virtual Flow Reserve (VFR) values, flow velocity, a pressure value, a maximum flow, a minimum flow, one or more fractional flow reserve (FFR) values, virtual fractional flow reserve values, coronary flow reserve (CFR) values, coronary flow velocity reserve (CFVR) values, instantaneous flow reserve (IFR) values, one or more index of myocardial resistance (IMR) values and a vascular resistance value, a combination of the foregoing, a weighted average of one or more of the foregoing and another value, and values derived from the foregoing.

Non-limiting Software Features and Embodiments for Implementing Stent Planning, Interface, and Other Features of Disclosure The following description is intended to provide an overview of device hardware and other operating components suitable for performing the methods of the disclosure described herein. This description is not intended to limit the applicable environments or the scope of the disclosure. Similarly, the hardware and other operating components may be suitable as part of the apparatuses described above. The disclosure can be practiced with other system configurations, including personal computers, multiprocessor systems, microprocessor-based or programmable electronic device, network PCs, minicomputers, mainframe computers, and the like. The disclosure can also be practiced in distributed computing environments where tasks are performed by remote processing devices that are linked through a communications network such as in different rooms of a catheter or cath lab.

The methods facilitate automatic stent planning using blood vessel data. This blood vessel data can include data from an intravascular pullback during which imaging data, which can include distance measurements to generate images, is obtained with regard to one or more blood vessels such as cardiac arteries. In one embodiment, the term "automatically" and "automatic" mean without human intervention. For example, a user can select a stent planning user interface icon or other input device or representation when using an intravascular data collection/diagnostic system. In response to that selection and any other user selections or input criteria, the system can then automatically generate one or more candidate virtual stents and the position thereof relative to a blood vessel representation displayed to the user. These candidate stent representations can be automatically generated for the user to consider as part of the stent deployment planning. Notwithstanding the foregoing, the scope of the terms discussed herein is not intended to be limiting, but rather to clarify their usage and incorporate the broadest meaning of the terms as known to those of ordinary skill in the art.

Some portions of the detailed description are presented in terms of methods such as algorithms and symbolic representations of operations on data bits within a computer memory. These algorithmic descriptions and representations can be used by those skilled in the computer and software related fields. In one embodiment, an algorithm is here, and generally, conceived to be a self-consistent sequence of operations leading to a desired result. The operations performed as methods stops or otherwise described herein are those requiring physical manipulations of physical quantities. Usually, though not necessarily, these quantities take the form of electrical or magnetic signals capable of being stored, transferred, combined, transformed, compared, and otherwise manipulated.

Unless specifically stated otherwise as apparent from the following discussion, it is appreciated that throughout the description, discussions utilizing terms such as "processing" or "computing" or "searching" or "indicating" or "detecting" or "measuring" or "calculating" or "comparing" or "clustering" or "intersecting" or "overlapping" or "generating" or "sensing" or "determining" or "displaying," or Boolean logic or other set related operations or the like, refer to the action and processes of a computer system, or electronic device, that manipulates and transforms data represented as physical (electronic) quantities within the computer system's or electronic devices' registers and memories into other data similarly represented as physical quantities within electronic memories or registers or other such information storage, transmission or display devices.

The present disclosure, in some embodiments, also relates to an apparatus for performing the operations herein. This apparatus may be specially constructed for the required purposes, or it may comprise a general purpose computer selectively activated or reconfigured by a computer program stored in the computer. Various circuits and components thereof can be used to perform some of the data collection and transformation and processing described herein.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear from the description provided herein. In addition, the present disclosure is not described with reference to any particular programming language, and various embodiments may thus be implemented using a variety of programming languages. In one embodiment, the software instructions are configured for operation on a microprocessor or ASIC of an intravascular imaging/blood vessel data collection system.

Embodiments of the disclosure may be implemented in many different forms, including, but in no way limited to, computer program logic for use with a processor (e.g., a microprocessor, microcontroller, digital signal processor, or general purpose computer), programmable logic for use with a programmable logic device, (e.g., a Field Programmable Gate Array (FPGA) or other PLD), discrete components, integrated circuitry (e.g., an Application Specific Integrated Circuit (ASIC)), or any other means including any combination thereof.

In a typical embodiment of the present disclosure, some or all of the processing of the data collected using an OCT probe, an IVUS probe, other imaging probes, an angiography system, and other imaging and subject monitoring devices and the processor-based system are implemented as a set of computer program instructions that is converted into a computer executable form, stored as such in a computer readable medium, and executed by a microprocessor under the control of an operating system. Thus, user interface instructions and triggers based upon the completion of a pullback or a co-registration request, for example, are transformed into processor understandable instructions suitable for generating intravascular data, performing image processing using various and other features and embodiments described above.

In addition, user interface commands, a user query, a system response, transmitted probe data, input data and other data and signal described herein are transformed into processor understandable instructions suitable for responding to user interface selections, controlling a graphical user interface, control and graphic signal processing, displaying cross-sectional information, rendered stents and guidewires and images from other data collection modalities, generating and displaying stents and indicators and other intravascular data, displaying OCT, angiography, detecting shadows, detecting peaks, and other data as part of a graphic user interface and other features and embodiments as described above. Data and parameters suitable for display as GUI components or controls, values, or as another representation in a graphical user interface can include without limitation guidewire, apposition bars, user interface panels, masks, stent struts, missing data representations, lumen curve data, shadows, angiography representations, three and two dimensional renders and views, data and images extracted from or derived using the foregoing and other features as described herein.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and internetworking technologies. The computer program may be distributed in any form as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the interne or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the internet or World Wide Web).

Various examples of suitable processing modules are discussed below in more detail. As used herein a module refers to software, hardware, or firmware suitable for performing a specific data processing or data transmission task. In one embodiment, a module refers to a software routine, program, or other memory resident application suitable for receiving, transforming, routing and processing instructions, or various types of data such as intravascular data, angiography data, OCT data, IVUS data, offsets, shadows, pixels, intensity patterns, taper angles, amount of taper, stent length, stent width, stent expansion, landing zone position, side branch orientation, cluster determination, cluster overlap/intersection analysis, stent orientation, stent position relative to side branch position, user interface data, control signals, angiography data, user actions, interferometer signal data, detected stents, candidate virtual stents, scores, SES values, VFR values, FFR values, lumen contours and other information of interest as described herein.

Computers and computer systems described herein may include operatively associated computer-readable media such as memory for storing software applications used in obtaining, processing, storing and/or communicating data. It can be appreciated that such memory can be internal, external, remote or local with respect to its operatively associated computer or computer system.

Memory may also include any means for storing software or other instructions including, for example and without limitation, a hard disk, an optical disk, floppy disk, DVD (digital versatile disc), CD (compact disc), memory stick, flash memory, ROM (read only memory), RAM (random access memory), DRAM (dynamic random access memory), PROM (programmable ROM), EEPROM (extended erasable PROM), and/or other like computer-readable media.

In general, computer-readable memory media applied in association with embodiments of the disclosure described herein may include any memory medium capable of storing instructions executed by a programmable apparatus. Where applicable, method steps described herein may be embodied or executed as instructions stored on a computer-readable memory medium or memory media. These instructions may be software embodied in various programming languages such as C++, C, Java, and/or a variety of other kinds of software programming languages that may be applied to create instructions in accordance with embodiments of the disclosure.

The term "machine-readable medium" or "computer-readable-medium" includes any medium that is capable of storing, encoding or carrying a set of instructions for execution by the machine and that cause the machine to perform any one or more of the methodologies of the present disclosure. While the machine-readable medium is shown in an example embodiment to be a single medium, the term "machine-readable medium" should be taken to include a single medium or multiple media (e.g., a database, one or more centralized or distributed databases and/or associated caches and servers) that store the one or more sets of instructions.

A storage medium may be non-transitory or include a non-transitory device. Accordingly, a non-transitory storage medium or non-transitory device may include a device that is tangible, meaning that the device has a concrete physical form, although the device may change its physical state. Thus, for example, non-transitory refers to a device remaining tangible despite this change in state.

The aspects, embodiments, features, and examples of the disclosure are to be considered illustrative in all respects and are not intended to limit the disclosure, the scope of which is defined only by the claims. Other embodiments, modifications, and usages will be apparent to those skilled in the art without departing from the spirit and scope of the claimed invention.

The use of headings and sections in the application is not meant to limit the invention; each section can apply to any aspect, embodiment, or feature of the invention.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise. As used herein, the term "about" refers to a ±10% variation from the nominal value.

It should be understood that the order of steps or order for performing certain actions is immaterial so long as the present teachings remain operable. Moreover, two or more steps or actions may be conducted simultaneously. The examples presented herein are intended to illustrate potential and specific implementations of the disclosure. It can be appreciated that the examples are intended primarily for purposes of illustration of the disclosure for those skilled in the art. There may be variations to these diagrams or the operations described herein without departing from the spirit of the disclosure. For instance, in certain cases, method steps or operations may be performed or executed in differing order, or operations may be added, deleted or modified.

Where a range or list of values is provided, each intervening value between the upper and lower limits of that range or list of values is individually contemplated and is encompassed within the invention as if each value were specifically enumerated herein. In addition, smaller ranges between and including the upper and lower limits of a given range are contemplated and encompassed within the invention. The listing of exemplary values or ranges is not a disclaimer of other values or ranges between and including the upper and lower limits of a given range.

Furthermore, whereas particular embodiments of the disclosure have been described herein for the purpose of illustrating the disclosure and not for the purpose of limiting the same, it will be appreciated by those of ordinary skill in the art that numerous variations of the details, materials and arrangement of elements, steps, structures, and/or parts may be made within the principle and scope of the disclosure without departing from the disclosure as described in the claims.

Furthermore, whereas particular embodiments of the disclosure have been described herein for the purpose of illustrating the disclosure and not for the purpose of limiting the same, it will be appreciated by those of ordinary skill in the art that numerous variations of the details, materials and arrangement of elements, steps, structures, and/or parts may be made within the principle and scope of the disclosure without departing from the disclosure as described in the claims.

What is claimed is:

1. A system for automated display of stent planning information comprising:
    an electronic memory device; and
    one or more processors in communication with the electronic memory device, wherein the memory comprises instructions executable by the one or more processors to cause the one or more processors to:

compute a set of lumen cross-sectional distance-based values from intravascular data generated using an intravascular probe pulled back through a blood vessel;

identify a set of local maxima from the set of lumen cross-sectional distance-based values, wherein one or more of the local maxima are correlated with potential stent landing zones;

determine one or more frames in the intravascular data that correspond to one or more of the local maxima;

determine, in connection with the set of local maxima, pairs of candidate stent landing zones by identifying one or more frames disposed at a boundary of a search window, wherein a size of search window is a length of one or more stents;

generate, for each pair of candidate landing zones, a stent effectiveness score (SES) that results from placement of a virtual stent of a given distance and length at each pair of candidate landing zones, wherein generating the SES for each pair of candidate landing zones comprises:

calculating, by the one or more processors, a first virtual fractional flow reserve (VFR) for the vessel prior to placing the virtual stent;

calculating a second Virtual Fractional Reserve for the vessel subsequent to placing the virtual stent;

determining a difference, by the one or more processors, between the first VFR and the second VFR to obtain a change in VFR in response to stent placement; and dividing, by the one or more processors, the change in VFR by a value based on the length of the virtual stent; and providing a display of at least one indication of a virtual stent defined by landing zones determined based on the stent effectiveness score, as well as an indication of an effect of the virtual stent.

2. The system of claim 1, wherein the lumen distance-based values are selected from a group consisting of a lumen area, a lumen radius, a lumen diameter, a lumen chord, and a distance that is measured from a point on a boundary of a lumen.

3. The system of claim 1 further comprising instructions executable by the one or more processors to cause the one or more processors to:

rank the stent effectiveness scores; and identifying one or more virtual stents, defined by landing zones determined based on ranking of the stent effectiveness scores, wherein the one or more virtual stents are displayed relative to a representation of a segment of the blood vessel.

4. The system of claim 1 further comprising instructions executable by the one or more processors to cause the one or more processors to: generate a representation of a stent having a stent length and displaying the representation of the stent disposed at a first landing zone and a second landing zone, wherein the first and the second landing zone correspond to the stent effectiveness score.

5. The system of claim 1 further comprising instructions executable by the one or more processors to cause the one or more processors to: adjust the SES with one or more weighting factors.

6. The system of claim 5 wherein the one or more weighting factors comprise one or more of: the quality of landing zone; total lumen area of all branches covered by the stent; amount of tapering of blood vessel; stent limits based on physician preference; and restrictions based on artery type.

7. The system of claim 1 further comprising instructions executable by the one or more processors to cause the one or more processors to: morph a representation of a vessel using a stent representation to compute a change in an intravascular parameter suitable for determining the SES.

8. The system of claim 1 wherein the one or more processors are further configured to select one or more virtual stents having SES with a predicted VFR above or equal to an end user set target VFR.

9. The system of claim 1, wherein the one or more processors are further configured to perform a cluster-based analysis of virtual stents that are bounded by the candidate landing zones, and wherein providing, for display, at least one indication of a virtual stent is based on the cluster-based analysis.

* * * * *